United States Patent

Robinson et al.

[11] Patent Number: 5,860,998
[45] Date of Patent: Jan. 19, 1999

[54] DEPLOYMENT DEVICE FOR TUBULAR EXPANDABLE PROSTHESIS

[75] Inventors: Timothy Robinson, Sandown, N.H.;
Michael F. Weiser, Groton, Mass.;
Dennis Kujawski, Brookline, N.H.;
Clifford J. Dwyer, Wilmington, Mass.

[73] Assignee: C. R. Bard, Inc., Murray Hill, N.J.

[21] Appl. No.: 756,061

[22] Filed: Nov. 25, 1996

[51] Int. Cl.⁶ .............................. A61M 29/00; A61F 2/06
[52] U.S. Cl. ...................... 606/194; 606/108; 606/191; 623/1
[58] Field of Search ........................ 623/1, 12; 606/191, 606/194, 195, 108

[56] References Cited

U.S. PATENT DOCUMENTS

| | | |
|---|---|---|
| 3,570,013 | 3/1971 | Blumen . |
| 3,657,744 | 4/1972 | Ersek . |
| 3,880,137 | 4/1975 | Bucalo . |
| 3,951,132 | 4/1976 | Bucalo . |
| 4,056,854 | 11/1977 | Boretos et al. . |
| 4,140,126 | 2/1979 | Choudhury . |
| 4,562,596 | 1/1986 | Kornberg . |
| 4,577,631 | 3/1986 | Kreamer . |
| 4,580,568 | 4/1986 | Gianturco . |
| 4,617,932 | 10/1986 | Kornberg . |
| 4,732,152 | 3/1988 | Wallsten et al. ......................... 606/108 |
| 4,768,507 | 9/1988 | Fischell et al. ......................... 606/108 |
| 4,892,539 | 1/1990 | Koch . |
| 4,969,891 | 11/1990 | Gewertz . |
| 4,990,151 | 2/1991 | Wallsten . |
| 4,994,071 | 2/1991 | MacGregor . |
| 4,998,539 | 3/1991 | Delsanti . |
| 5,007,926 | 4/1991 | Derbyshire . |
| 5,019,090 | 5/1991 | Pinchuk . |
| 5,035,706 | 7/1991 | Gianturco et al. . |
| 5,047,050 | 9/1991 | Arpesani . |
| 5,059,205 | 10/1991 | El-Nounou et al. . |
| 5,104,399 | 4/1992 | Lazarus . |
| 5,104,404 | 4/1992 | Wolff . |
| 5,151,105 | 9/1992 | Kwan-Gett . |
| 5,197,951 | 3/1993 | Mahurkar . |
| 5,197,978 | 3/1993 | Hess . |
| 5,207,695 | 5/1993 | Trout, III . |
| 5,211,658 | 5/1993 | Clouse . |
| 5,219,355 | 6/1993 | Parodi et al. . |
| 5,222,971 | 6/1993 | Willard et al. . |
| 5,242,452 | 9/1993 | Inoue . |
| 5,242,462 | 9/1993 | El-Nounou et al. . |
| 5,275,622 | 1/1994 | Lazarus et al. . |
| 5,282,824 | 2/1994 | Gianturco . |
| 5,290,295 | 3/1994 | Querals et al. . |
| 5,290,310 | 3/1994 | Makower et al. . |
| 5,318,586 | 6/1994 | Ereren . |
| 5,354,308 | 10/1994 | Simon et al. . |
| 5,360,443 | 11/1994 | Barone et al. . |
| 5,366,504 | 11/1994 | Anderson et al. . |
| 5,375,612 | 12/1994 | Cottenceau . |
| 5,383,892 | 1/1995 | Cardon et al. . |
| 5,387,235 | 2/1995 | Chuter . |
| 5,391,172 | 2/1995 | Williams et al. . |
| 5,417,708 | 5/1995 | Hall et al. . |
| 5,425,756 | 6/1995 | Heil, Jr. et al. . |
| 5,456,695 | 10/1995 | Dallemagne . |
| 5,456,713 | 10/1995 | Chuter . |
| 5,464,449 | 11/1995 | Ryan et al. . |
| 5,480,423 | 1/1996 | Ravenscroft et al. . |
| 5,489,295 | 2/1996 | Piplani et al. . |
| 5,509,931 | 4/1996 | Schmitt . |
| 5,562,726 | 10/1996 | Chuter ..................................... 606/195 |
| 5,591,195 | 1/1997 | Taheri . |
| 5,603,698 | 2/1997 | Roberts et al. ........................... 606/191 |
| 5,605,530 | 2/1997 | Fischell et al. ............................... 600/3 |
| 5,628,788 | 5/1997 | Pinchuk . |
| 5,639,278 | 6/1997 | Dereume et al. . |
| 5,653,743 | 8/1997 | Martin . |
| 5,702,418 | 12/1997 | Ravenscroft ................................. 623/1 |

FOREIGN PATENT DOCUMENTS

| | | |
|---|---|---|
| 0466518 | 1/1992 | European Pat. Off. . |
| 0472731 | 3/1992 | European Pat. Off. . |
| 0539237 | 4/1993 | European Pat. Off. . |
| 0646365 | 4/1995 | European Pat. Off. . |
| 0657147 | 6/1995 | European Pat. Off. . |
| 0696447 | 2/1996 | European Pat. Off. . |
| 0701800 | 3/1996 | European Pat. Off. . |
| 2722678 | 1/1996 | France . |
| 1482672 | 5/1989 | U.S.S.R. . |
| 1641290 | 4/1991 | U.S.S.R. . |
| WO 8908433 | 9/1989 | WIPO . |
| WO 9508966 | 4/1995 | WIPO . |

| | | |
|---|---|---|
| WO 9509586 | 4/1995 | WIPO . |
| WO 9534255 | 12/1995 | WIPO . |
| WO 9623455 | 8/1996 | WIPO . |
| WO 9624308 | 8/1996 | WIPO . |
| WO 9717911 | 5/1997 | WIPO . |
| WO 9717912 | 5/1997 | WIPO . |
| WO 9717913 | 5/1997 | WIPO . |
| WO 9726936 | 7/1997 | WIPO . |

OTHER PUBLICATIONS

Rollins et al., "Self Expanding Metallic Stents: Preliminary Evaluation . . . ", Radiology, Jun. 1987, pp. 739–742.

Mirich et al., "Percutaneously Placed Endovascular Grafts for Aortic Aneurysms . . . ", Radiology, Mar. 1989, pp. 1033–1037.

Lawrence, Jr. et al., "Percutaneous Endovascular Graft: Experimental Evaluation", Radiology, May 1987, pp. 357–360.

Dobben et al., "Prostatic Urethra Dilatation with the Gianturco Self–Expanding Metallic Stent . . . ", AJF, Apr. 1991, pp. 757–761.

Irie et al., "Relocatable Gianturco Expandanble Metallic Stents", Radiology, vol. 178, No. 2, pp. 575–578.

Yoshioka et al., Self–Expanding Endovascular Graft: An Experimental Study in dogs, AJR:151, Oct. 1988, pp. 673–676.

A Self–Expanding Bifucated Endovascular Graft for Abdominal Aortic Aneurysm Repair, An Initial Study in a Canine Model, J ASAIO. vol. 42, Wilson et al., Sep. 1996, pp. M386–M393.

Resection and Reconstruction of the Carotid Bifurcation with Polytetrafluoroethylene Grafts; Operative Techniques, J Coardiovasc Surg. vol. 32, issue 4, Castellani et al., 1991, pp. 426–435.

Use of a Ringed Intraluminal Graft in the Operative Management of Abdominal Aortic Aneurysms, J Surg. vol. 72, issue 10, Cave–Bigley et al., Oct. 1985, pp. 825–827.

Large Diameter Expanded Polytetrafluoroethylene Grafts for Infrarenal Aortic Aneurysm Surgery, J Cardiovasc Surg. vol. 31, issue 6, Corson, et al., 1990, pp. 702–705.

Infrarenal Aortic Aneurysm Structure: Implications for Transfemoral Repair, J Vasc Surg. vol. 20, issue 1, Chuter et al., Jul. 1994, pp. 44–50.

Bifurcated ("Y") Internal Thoracic Coronary Artery Grafts, J Thorac Cardiovasc Surg. vol. 103, issue 3, Olearchyk et al., Mar. 1992, p. 601.

Bifurcated ("Y") Internal Thoracic Coronary Artery Grafts, J Thorac Cardiovas Surg. vol. 106, issue 5, van Son et al., Nov. 1993, pp. 945–946.

A Clinical Survey of Aortobifemoral Bypass Using Two Inherently Different Graft Types, Ann Surg. vol. 208, issue 5, Cintora et al., Nov. 1988, pp. 625–630.

Late Iliac Artery Aneurysms and Occulusive Disease After Aortic Tube Grafts for Abdominal Aortic Aneurysm Repair, Ann Surg. vol. 214, issue 6, Calcagno et al., Dec. 1991, pp. 733–736.

Transfermoral Insertation of a Bifucated Endovascular Graft for Aortic Aneurysm Repair: The First 22 Patients, J Cardiovasc Surg. vol. 3, issue 2, Chuter et al., Apr. 1995, pp. 121–128.

The Role of Endovascular Grafting Technique in the Treatment of Infrarenal Abdominal Aortic Aneurysm, J Cardiovasc Surg. vol. 3, issue 2, Moore, Apr. 1995, pp. 109–114.

Bifurcated Stent–Grafts for Endovascular Repair of Abdominal Aortic Aneurysm, J Surg. Endosc. vol. 8, issue 7, Chuter et al., Jul. 1994, pp. 800–802.

Bifurcated Grafts in the Aorto–Femoral Tract, J Cardiovasc Surg., Manresa, et al., 1973, pp. 509–513.

Transfermoral Endoluminal Repair of Abdominal Aortic Aneurysm with Bifurcated Graft, Lancet. vol. 344, issue 8923, Yusuf et al., Sep. 3, 1994, pp. 650–651.

Evolution of Technologies in Endovascular Grafting, J Cardiovasc Surg. vol. 3, issue 2, Green et al., Apr. 1995, pp. 101–107.

*Primary Examiner*—Paul B. Prebilic
*Attorney, Agent, or Firm*—Arthur Z. Bookstein

[57] ABSTRACT

An endoprosthetic implant is formed from a plurality of separate individual components that are inserted sequentially and transluminally into a bifurcated vascular region with each component being deployed in sequence by a sequence of catheter-like deployment devices. The separate components are placed relative to each other to define a bifurcated endoprosthesis. In one embodiment the deployment device includes a tubular sheath for maintaining the radially expandable tubular implant in a contracted configuration and a gripping device including a cup and a gripping member that cooperate to define an annular space by which the trailing end of the implant can be securely held by the deployment device during positioning of the device.

1 Claim, 14 Drawing Sheets

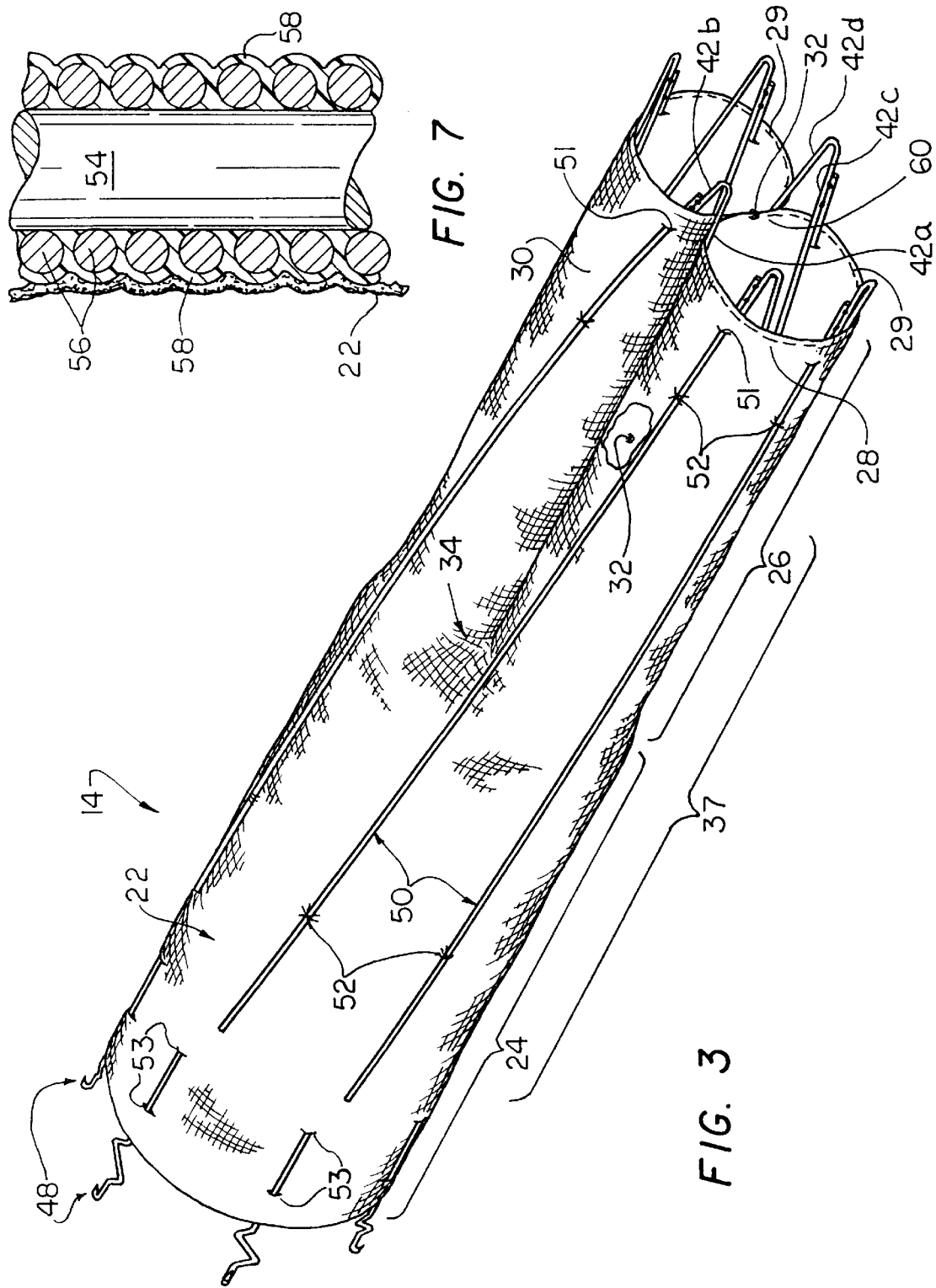

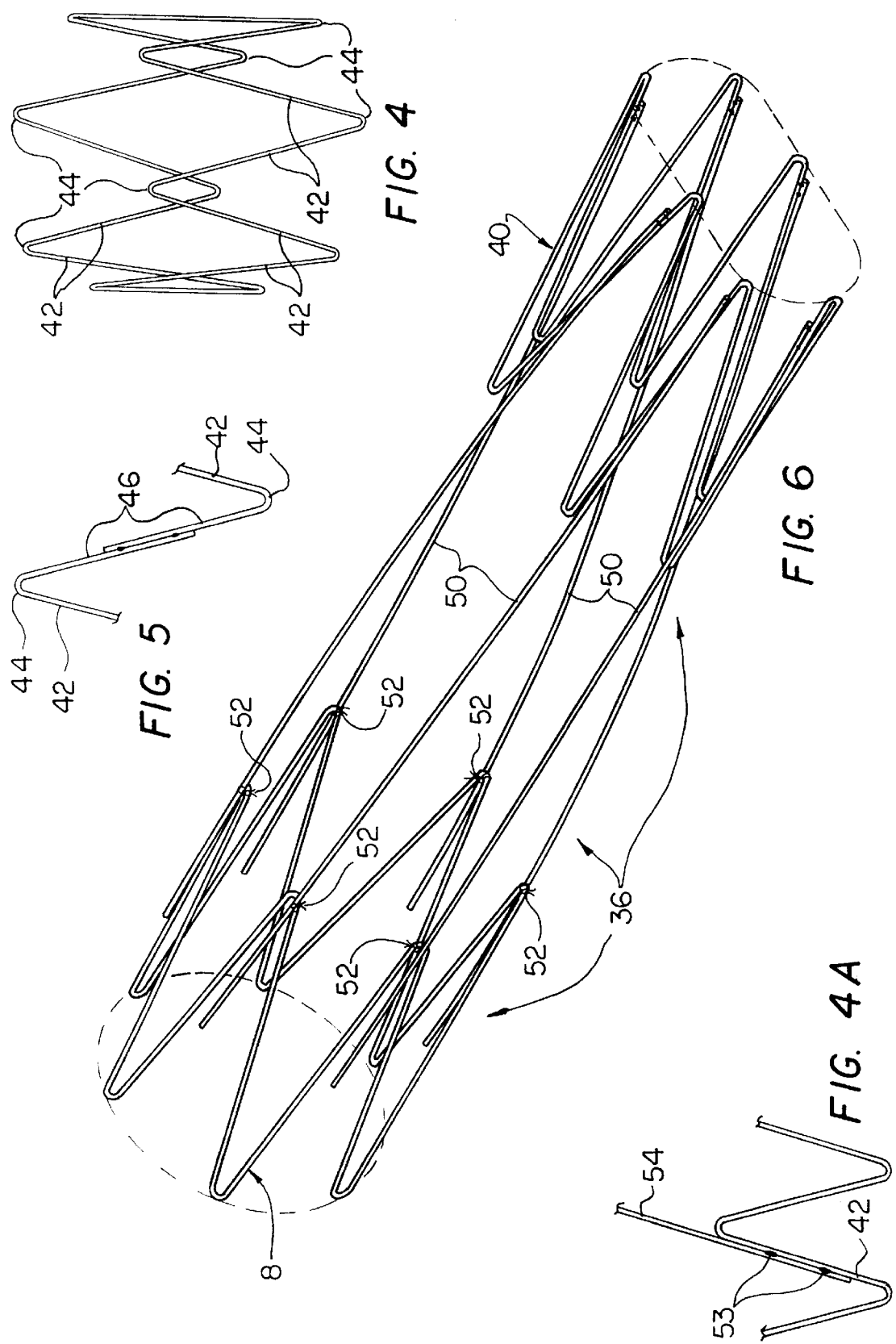

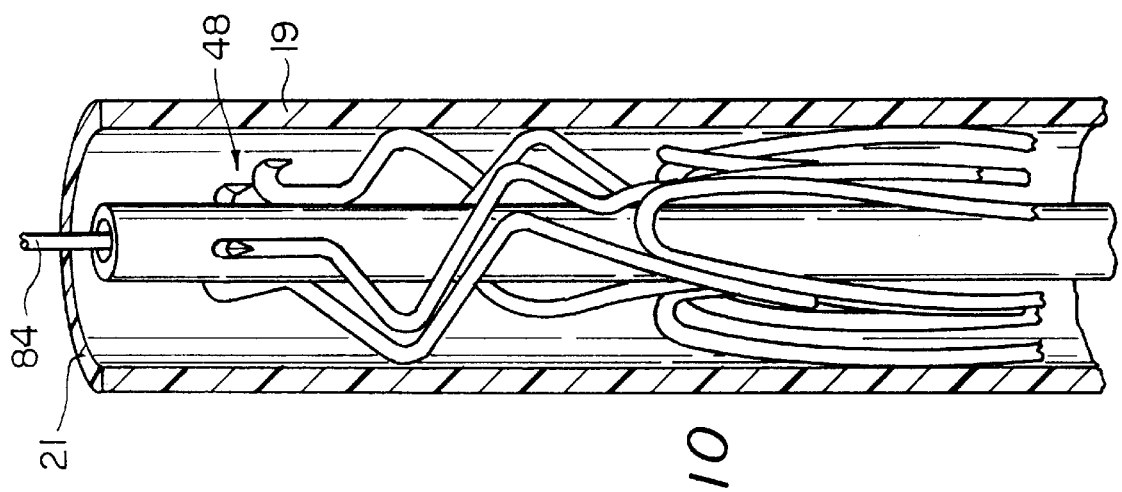
FIG. 10
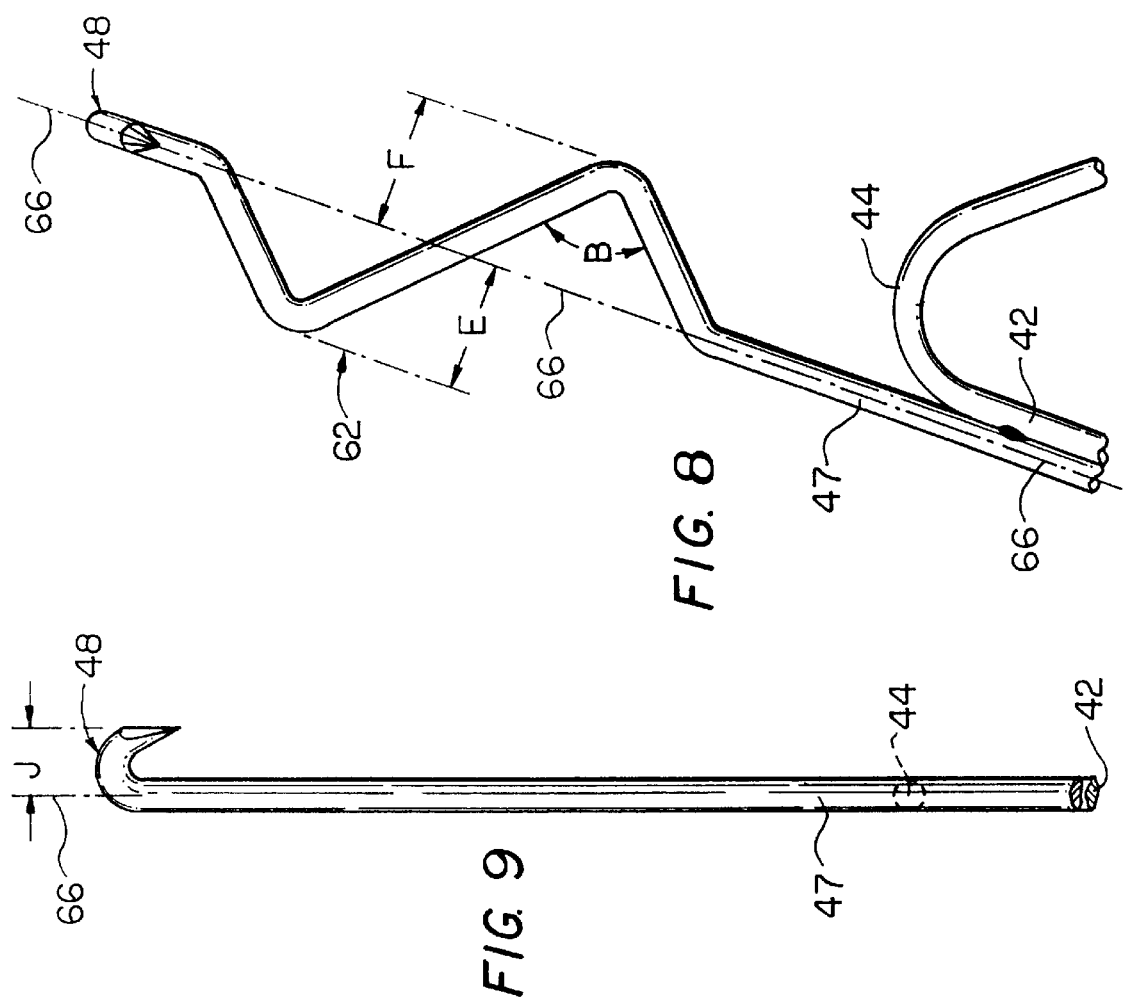
FIG. 8
FIG. 9

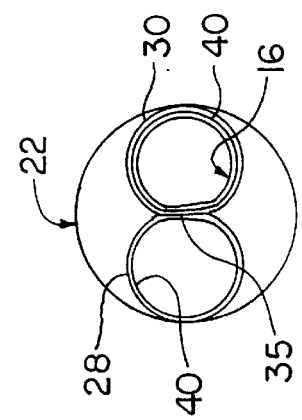
FIG. 18
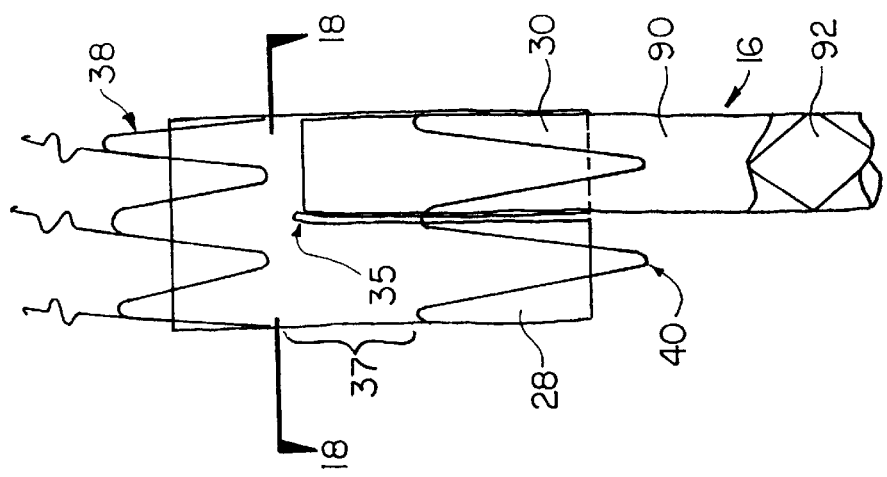
FIG. 17
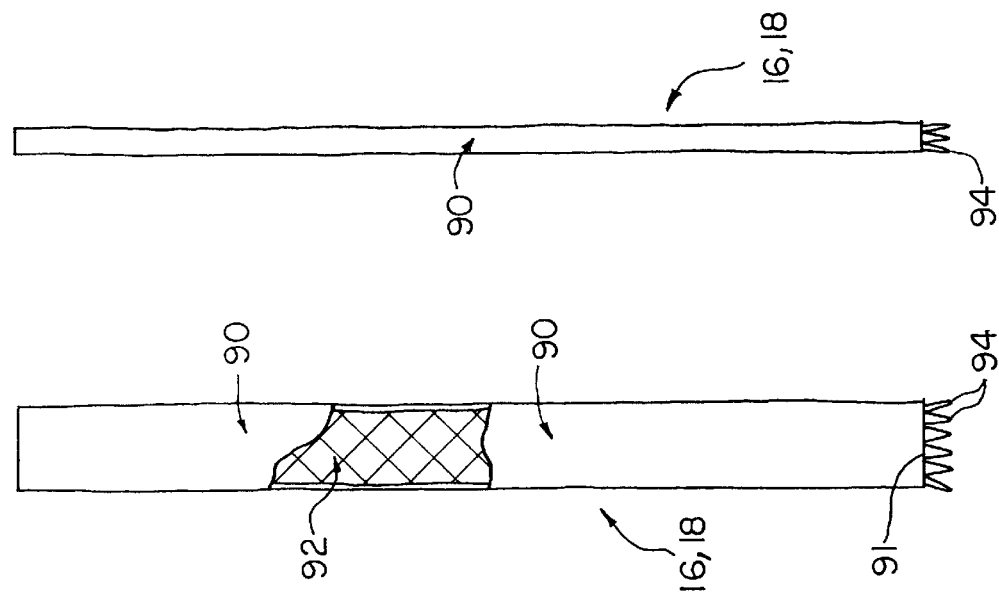
FIG. 15
FIG. 16

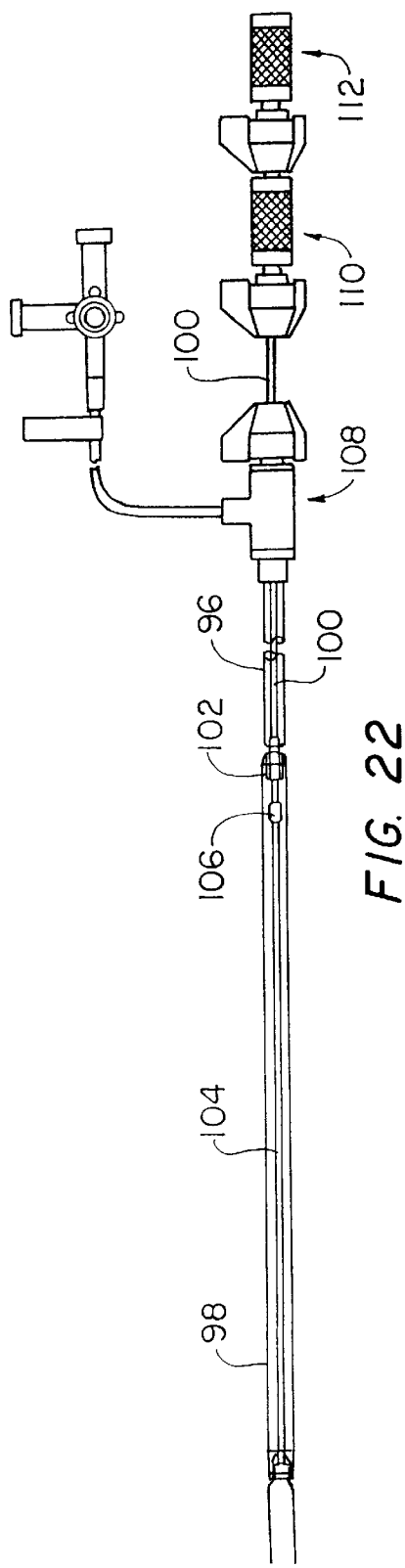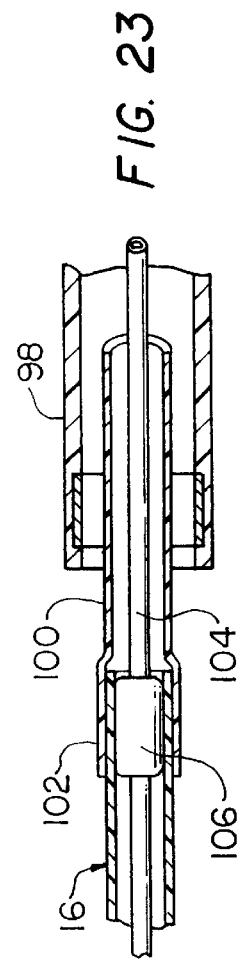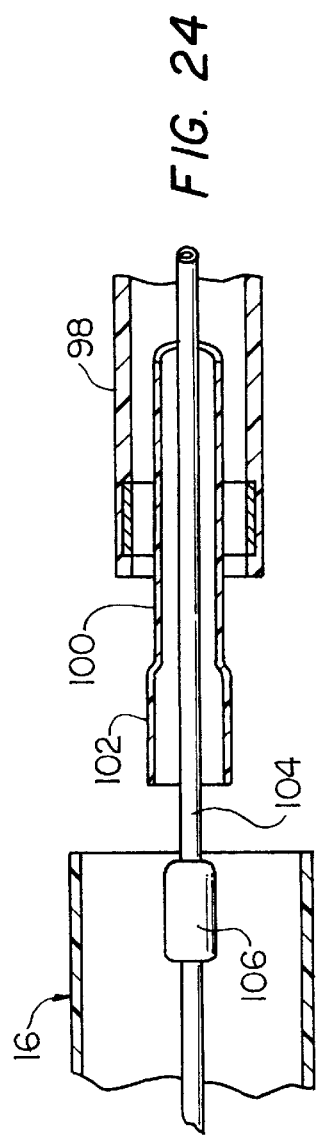

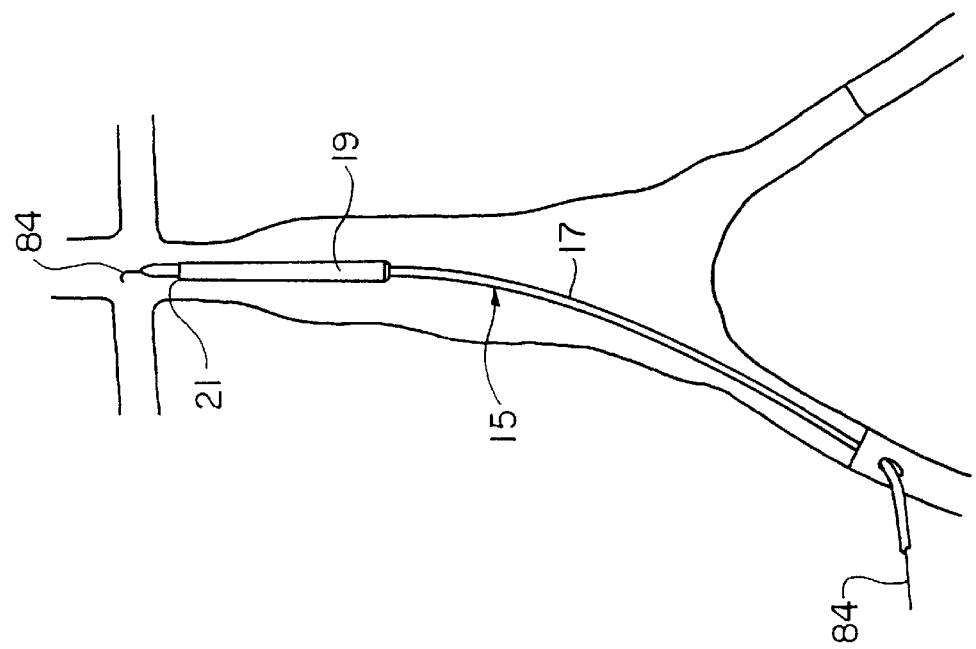
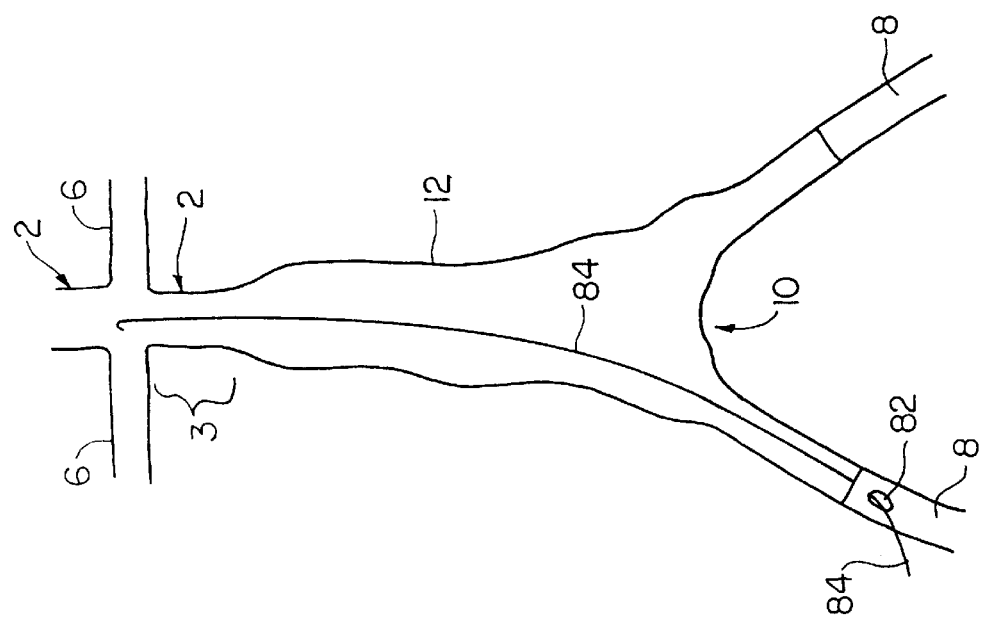

DEPLOYMENT DEVICE FOR TUBULAR EXPANDABLE PROSTHESIS

FIELD OF THE INVENTION

The invention relates to devices and techniques for placing and securing an endoprosthesis in a patient's vascular system, including bifurcated blood vessels.

BACKGROUND OF THE INVENTION

Among the long accepted practices to treat a variety of vascular disorders are surgical procedures that involve placement of a tubular graft in a patient's blood vessels. The construction and characteristics of the graft typically are adapted to optimize its use in the specific surgical environment and condition to be treated and, accordingly, a number of different types of grafts are available. Among the most common vascular grafts are those formed from a woven or knitted tubular fabric as well as non-fabric tubes such as expanded polytetrafluoroethylene. Such grafts typically are placed in a patient's vascular system in a highly invasive surgical procedure. In general, the complexity of the surgical procedure required to place the graft will depend on many factors, including the location and surgical accessibility of the portion of the patient's vasculature where the graft is to be placed.

Not all vascular conditions in which it would be desirable to place a graft can be so treated. Among the particularly troublesome medical conditions in which it is desirable to place a graft is that of an abdominal aortic aneurysm, in which a portion of the patient's aorta, the major artery carrying blood from the heart, has developed a weakened wall such that the weakened portion will tend to expand under the influence of the patient's blood pressure. An aortic aneurysm presents a life threatening risk that the aneurysm may burst causing massive internal bleeding. Treatment of the condition typically has involved deeply invasive abdominal surgery in which the patient's abdominal cavity is opened to reach and expose the aortic aneurysm. While maintaining the patient on an independent life support system, the region of the aneurysm is incised lengthwise to enable insertion of the graft into the aorta to span the weakened region and define a structurally strong tubular flow path between the remaining healthy portions of the aorta. The graft, so positioned, then is sutured in place. The graft thus serves as a reinforcing liner for the weakened portion of the aorta. Such surgical procedures have been characterized by a relatively high mortality rate. Typically, patients suffering from the condition are elderly and are less able to survive the rigors of major abdominal surgery. Additionally, there is a substantial degree of risk when the abdominal cavity is opened because the confining pressure of other abdominal organs on the aorta is released. In some cases, the aortic wall in the region of the aneurysm is so weak that upon release of the confining pressure, the aneurysm may burst with resulting immediate massive hemorrhaging.

Significant effort has been directed to the development of less invasive techniques for placement of a graft, such as in the abdominal aortic region, in a manner that presents less risk to the patient. Various devices in the form of a single tubular implant have been described for that purpose. Typically, such single tube devices have a means for anchoring the ends of the graft to healthy vascular tissue at the opposite ends of the aneurysmal region.

In the case of abdominal aortic aneurysms, however, by the time the aneurysm is discovered, it may have advanced to a stage where there is insufficient healthy tissue in the region where the aorta bifurcates into the two iliac arteries for the end of a single tubular graft to be secured. Often the aneurysm has advanced into and involves the iliac arteries as well. Such a condition cannot be treated by a single lumen tubular prosthesis. If an endoluminal prosthesis is to be placed in such anatomy, the prosthesis must have a bifurcated configuration in order to extend fully through the regions of aneurysm in all of the involved arteries and with the device being in secure engagement with healthy tissue to insure that it provides full endoluminal support and will not migrate from its implanted position.

The necessity for the use of a bifurcated graft has been recognized. One approach is described in U.S. Pat. No. 5,489,295 (Piplani) in which a one-piece bifurcated graft is described as being placed in the bifurcated region of the aorta and iliac arteries. The procedure described is complex and requires many difficult manipulations by the physician. Additionally, the unpredictable variations and vascular anatomy of an individual patient can be expected to present blood vessels of shapes and diameters that do not readily match the preformed configuration of a one piece, preformed, bifurcated graft. Consequently, the use of such a graft is likely to result in mismatches between one or more of the three legs of the bifurcated graft with the corresponding aorta and iliac arteries.

Another device is described in PCT patent application PCT/US95/01466 (International Publication No. WO95/21592) in which a bifurcated device is formed in two sections, one of which includes a graft having a main body and one integral leg extension. The main body is intended to be placed in the aorta and the extension in one of iliac arteries. The main body also has an opening adjacent the leg extension that can be aligned with the other iliac artery. The second section of the device includes a tubular graft that can be advanced through the other iliac artery into engagement with the opening in the main body. This arrangement also is awkward to place and presents additional difficulties. Among those difficulties is that where the body and one of the legs is formed in a unitary structure, the device similarly does not lend itself to modular construction in which the individual components can be combined to match the dimensions of the particular patient's anatomy. Also among the difficulties with the device is that it employs stenting elements formed from a shape memory alloy that is not readily visualized under fluoroscopic examination and must be placed relatively quickly, before the stent expands as a consequence of exposure to body temperature.

A third approach, described in PCT application PCT/DK94/00468 (International Publication No. WO95/16406) employs an endovascular device for placement at the region of an arterial bifurcation that includes a three-component system including a main, bag-like body intended for placement in the aorta. The bag-like body has a pair of openings formed at its lower end. Each of the openings is said to receive an end of a tubular prosthesis inserted through each of the iliac arteries. The tubular prostheses are said to attach to the main bag-like body and extend into the iliac arteries. Among the apparent difficulties with this arrangement are that there is no way for the physician to visualize, fluoroscopically, the main bag-like body or the location of the openings that must be accessed in order to insert the leg segments into the openings. Additionally, the apparently flexible structure of the bag-like body would enable the bag to flex under the influence of blood flow, body movement and engagement with the apparatus for delivering and placing the leg segments, all of which would present considerable difficulties in the placement process. Moreover, even if the leg segments could be attached to the main body, the apparent relationship of the leg segments with the main body is such as to present an irregular, turbulent flow path from the main body to the leg extensions.

None of the prior art relating to the placement of a bifurcated tubular endoprosthetic implant within the region of the aortic-iliac arteries has suggested a modular construction by which the components can be accurately positioned, assembled and, if necessary, is recaptured within the delivery device so that the module can be redeployed in its proper position or removed in its entirety. Additionally, none embodies an arrangement in which the leg portions of the stent have a high degree of flexibility in order to conform easily to the configuration of the particular patient's vascular anatomy.

It would be desirable to provide a modular implant that can be constructed in situ with modules that can be accurately placed and connected easily with individual modules selected to conform closely to the vascular anatomy of the individual patient. It is among the general objects of the invention to provide such a modular implant construction.

SUMMARY OF THE INVENTION

The endoprosthetic implant of the present invention is formed from separate components that are individually and sequentially inserted transluminally to the region to be treated such as, for example, the region of the abdominal aorta and iliac arteries. Each is deployed in sequence by a catheter-like delivery device. Except for the first placed module, each module is connected to a previously placed module. The first placed module comprises a trunk adapted to be placed in the aorta and having a relatively large upstream opening and a pair of smaller downstream openings. Each of the downstream openings is adapted to receive the upstream end of one of two tubular leg extensions. The trunk, which is constructed to be recapturable within the delivery device, includes a tubular synthetic graft having upstream and downstream ends and a resilient expandable frame assembly. The frame assembly includes a radially expandable anchor at its upstream end that serves to secure the endoprosthesis to healthy aortic tissue and also maintains the upstream end of the endoprosthesis expanded and in sealed engagement with the lumen of the aorta. A stent at the downstream end of the graft maintains the downstream branches of the graft open and receptive to the leg extensions. The anchor and the stent are connected to each other by at least two longitudinal struts in a manner that enables the trunk to be recaptured within the delivery device and repositioned or removed. The struts, anchor and stent also provide sufficient longitudinal stiffness and column strength for the trunk so that it will not buckle when engaged by the leg extensions or the delivery device by which the leg extensions are placed. The frame assembly is such that the trunk is relatively stiff to assure that it will remain securely in place to present a stable target that can be accessed by the other modular components with improved facility. The leg extensions are constructed to facilitate their bending without kinking in order to conform to the specific anatomy of the patient. The modular construction of the endoprosthesis enables it to be formed from components, each of which can be selected to fit the specific part of the vascular anatomy of the patient into which it is to be placed.

It is among the general objects of the invention to provide an improved endoluminal implant adapted to be placed in a bifurcated vascular region.

Another object of the invention is to provide an arrangement of modular endoluminal implant components by which an endoluminal graft may be constructed within the vascular lumen to a configuration conforming to the patient's vascular anatomy.

Another object of the invention is to provide an arrangement of modular endoluminal implant components including a trunk for placement within a blood vessel and legs connectible to the trunk for individual placement in a branch blood vessels.

An additional object of the invention is to provide a modular graft of the type described in which each of the individual modules can be positioned accurately and in which at least the first placeable module can be recaptured and repositioned, if necessary.

Another object of the invention is to provide an improved method for construction of an endoluminal inplant in situ at a bifurcated region.

DESCRIPTION OF THE DRAWINGS

The foregoing and other object and advantages of the invention will be appreciated more fully from the following further description thereof, with reference to the accompanying drawings, of which:

FIG. 3 is an illustration of the trunk module of the endoprosthetic implant;

FIG. 4 is an illustration of an individual resilient component that may be used as an anchor or a stent;

FIG. 4A is an illustration of the region of connection between a strut and a straight segment of the stent;

FIG. 5 is an illustration of the juncture of the ends of the wire that forms the resilient component of FIG. 4;

FIG. 6 is an illustration of the frame assembly for the trunk component of the implant, including an anchor, a stent and a plurality of longitudinal struts extending between the anchor and stent;

FIG. 7 is a greatly enlarged longitudinal section of a portion of a strut of the trunk;

FIG. 8 is an illustration of an embodiment of a hook and hook support attached to a portion of the anchor as seen from a location radially outward of the anchor and viewed in a radially inward direction;

FIG. 9 is an illustration of the hook and hook support of FIG. 8 as seen from the left of FIG. 8 and as viewed in a direction generally tangential of the anchor;

FIG. 10 is an illustration of an anchor having the hook configuration illustrated in FIGS. 8 and 9 as withdrawn into a pod at the distal end of a delivery device;

FIG. 15 is an illustration of an embodiment of a leg extension that may be used in the practice of the invention, shown in its low profile, unexpanded configuration;

FIG. 16 is a fragmented illustration of the leg segment shown in FIG. 15 after being expanded; and FIG. 17 is an illustration of the manner in which the upstream end of a leg extension engages the trunk when the two are connected;

FIG. 18 an illustration as seen along the line 18—18 of FIG. 17;

FIG. 22 is a fragmented illustration of a deployment catheter having a modified arrangement for releasably gripping the trailing end of an endoprosthesis module;

FIG. 23 is a fragmented, sectional, diagrammatic illustration of the endoprosthesis gripping arrangement of FIG. 22, enlarged, and illustrating the gripping members projected distally of the end of the delivery sheath;

FIG. 24 is an illustration similar to FIG. 23 with the gripping mechanism having been operated to release the trailing end of the endoprosthesis and with the endoprosthesis as shown in an expanded configuration;

FIGS. 25A–25F illustrate, schematically, sequential steps in the placement of the endoprosthesis;

DESCRIPTION OF THE PREFERRED EMBODIMENT

Figure 1:
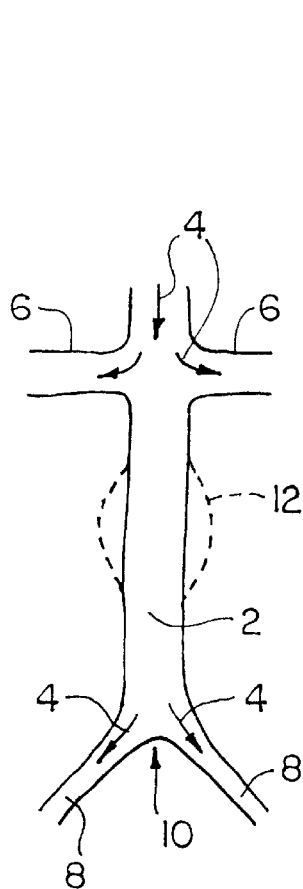
FIG. 1 is a diagrammatic illustration of a portion of an abdominal aorta illustrating, in phantom, an aortic aneurysm confined to the aorta.

FIG. 1 illustrates, diagrammatically, the region of the human aorta 2 through which oxygenated blood is pumped from the heart in a downstream direction suggested at the arrows 4. Also shown are the renal arteries 6 that branch off of the aorta to direct blood to the kidneys and the iliac arteries 8 that branch at a bifurcation 10 to serve the lower extremities. FIG. 1 also illustrates diagrammatically, and in phantom, an aneurysm 12 as may develop in the aorta 2 between the renal artery 6 and the bifurcation 10. The aneurysm 12 defines a weakened region of the wall of the aorta and may be susceptible to rupture and subsequent hemorrhaging under the influence of arterial blood pressure. Such a condition may be treated by placement of an implant within the artery to line and reinforce the artery in the region of the aneurysm 12. The condition has been treated, if at all, by attempting to place the implant surgically. Surgical placement presents a high risk to the patient. The present invention is directed to placement of an implant assembly endoluminally by radially contracting the implant within a sheath of a delivery catheter, inserting the catheter into a blood vessel to access the aneurysm, positioning the device within the aneurysm and then releasing the implant assembly into engagement with supportive, healthy arterial tissue beyond each end of the aneurysm.

In this description, a direction along which the delivery device is advanced (i.e., toward the heart) will be referred to variously as "leading", "forward", "above" or "renal" and the opposite direction will be referred to variously as "trailing", "rearward", "below" or "iliac". Thus the tubular implants may be considered as having a leading end and a trailing end. When an implant has been advanced into and through the blood vessel from a downstream location to an upstream deployment location, the leading end of the implant also may be considered as being "upstream" and the trailing end as "downstream". For a device advanced in an upstream-to-downstream direction, the leading-trailing convention would be reversed.

Figure 2:
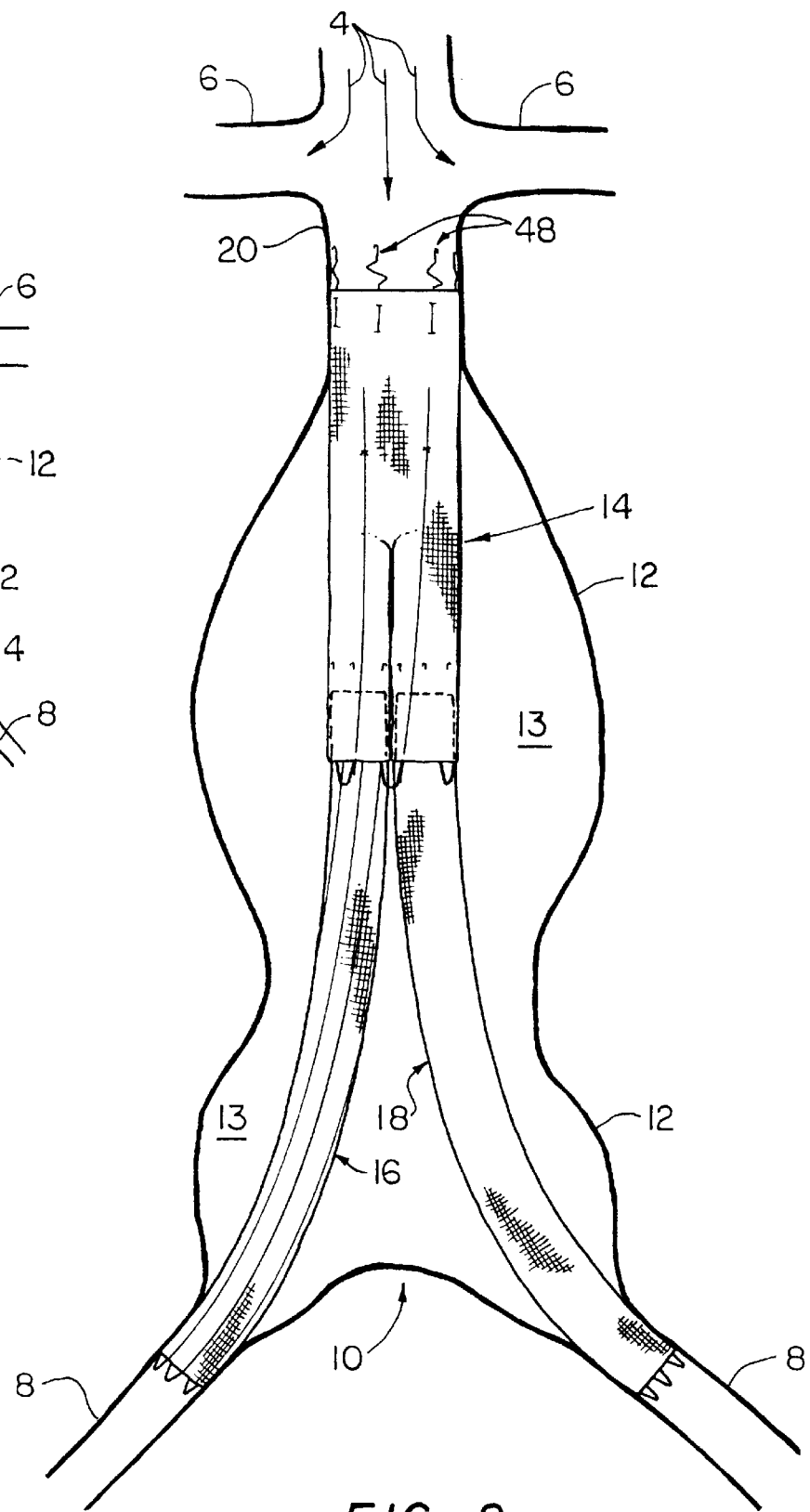
FIG. 2 is an enlarged illustration similar to FIG. 1 but with an aneurysm that has involved a substantial length of the abdominal aorta and has extended into the iliac arteries, with an implant in accordance with the invention operatively positioned in the region of the aneurysm.
Figure 11:
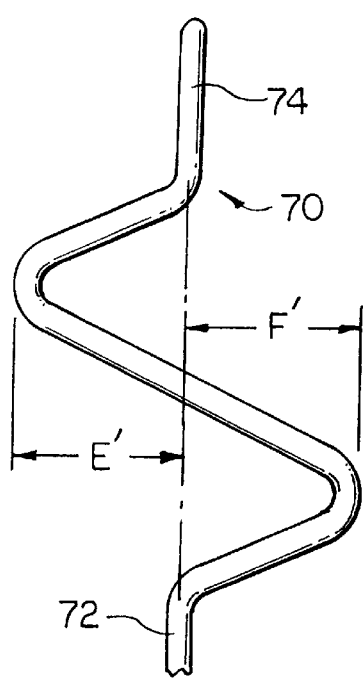
FIG. 11 is an illustration similar to FIG. 8 of a detent carried by the anchor at the upper end of the trunk engagable with the tissue of a body lumen to prevent movement of the anchor in an upstream direction after the endoprosthesis has been deployed.
Figure 12:
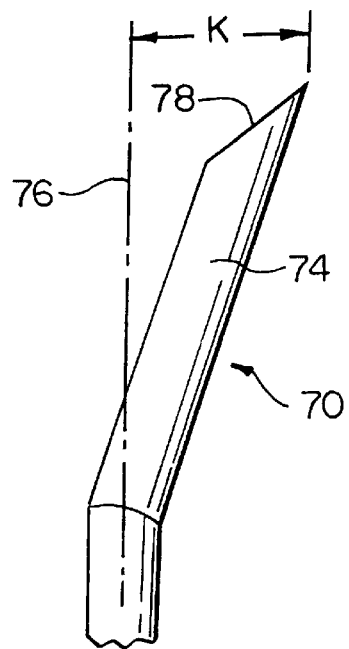
FIG. 12 is an enlarged side elevation of the bent tip at the end of the detent of FIG. 11.
Figure 13:
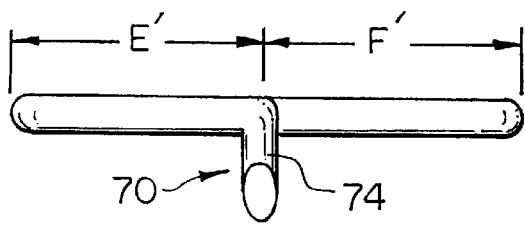
FIG. 13 is a top view of the detent arrangement of FIG. 11.

It is not uncommon for the presence of an aneurysm to be undetected for a significant time, during which the extent of the aneurysm may increase. The aneurysm may develop both upstream and downstream along the abdominal aorta, extending into or beyond the bifurcation 10 into one or both of the iliac arteries 8. FIG. 2 represents such a condition in which the aneurysm has developed at its lower end to include involvement with both iliac arteries 8. When an aneurysm has developed to that stage, there no longer is sufficient healthy tissue to be securely engaged by a single tubular implant. Consequently, if the condition is to be treated by endoluminal placement of a prosthesis, the prosthesis will have to extend into one or both of the branch vessels.

FIG. 2 illustrates the assembled and deployed modules of an implant in accordance with the invention. The modules include a trunk, indicated generally at 14, and a pair of legs extensions, indicated generally at 16, 18. The trunk 14 is adapted to securely engage a region of healthy, supportive arterial tissue 20 above the aneurysm 12. When deployed, the lower end of the trunk 14 extends into the region of the aneurysm and is arranged to receive the upper ends of leg extensions 16 and 18 in a secure connection. The lower ends of the leg extensions 16, 18 are arranged to extend into and engage healthy tissue in the iliac arteries. When the endoprosthetic implant is fully deployed, it will define flow channels for blood from healthy vessel tissue above the aneurysm to healthy vessel tissue below. Over time, and depending on the construction of the implant, tissue can be expected to grow into the wall of the implant and ultimately approximate a natural biological luminal surface. The region 13 within the aneurysm exteriorly of the implant typically can be expected to be filled with mural thrombus.

Each of the trunk 14 and leg extensions 16, 18 is placed endoluminally and separately, with the trunk 14 being placed first. The components are generally tubular and may be placed with a catheter-like delivery device, indicated diagrammatically at 15 in FIG. 19B, as described in European patent application 95114543.2 published Mar. 20, 1996 (Publication No. EP 701800A1), the disclosure of which is incorporated herein by reference, in its entirety. The delivery device 15 includes an elongate flexible tubular sheath 17 that defines a tubular pod 19 at its leading end. The pod 19 is adapted to contain an expandable tubular endoprosthesis, such as a trunk 14 or one of the leg extensions 16, 18, in a radially contracted, low profile configuration. When the delivery device 15 has been advanced to the intended site of deployment, the tubular endoprosthesis is maintained in position by a staying member (not shown) disposed within the sheath while the delivery sheath and pod are withdrawn. As the sheath and pod withdraw, the leading end of the endoprosthesis is progressively exposed and progressively expands into engagement with the blood vessel. The delivery device and trailing end of the endoprosthesis are configured so that they remain attached to the delivery device 15 until the physician has had an opportunity to confirm that the endoprosthesis is in its desired position and orientation. The physician then can complete withdrawal of the sheath and pod to completely release the implant in the patient. Alternately, if the implant is not in the desired position for orientation, the sheath can be readvanced forwardly to recapture the endoprosthesis for repositioning or removal from the patient.

One embodiment of the trunk component 14 of the invention is illustrated in FIG. 3. The trunk 14 includes an elongate flexible tubular graft 22 that may be of woven or other conventional vascular graft construction. The graft 22 of the trunk 14 preferably is bifurcated to include an upper single lumen portion 24 having a relatively large expanded diameter and a lower two-lumen portion 26 that includes bifurcated first and second branch tubes 28, 30. The techniques for constructing grafts having such a bifurcated structure are well known to those skilled in the art. Preferably the graft is of woven construction. Although the graft 22 includes the bifurcated branches 28, 30, the graft 22 is relatively short and is not intended itself to extend to the iliac arteries 8. Rather, the trunk 14 is constructed and selected so that the lower ends of the tubes 28, 30 will be disposed within the aneurysm, above the arterial bifurcation 10 and iliac arteries 8.

The trunk 14 should be formed to present a symmetrical internal configuration within its flow lumens, particularly in the bifurcated region 34. The bifurcate region 34 should define a relatively thin, smooth edge 35 (see FIGS. 17, 18) to the blood stream to minimize turbulence or regions of blood stagnation and to assure that the blood flow will be balanced and symmetrical in each of the legs 28, 30. Lack of symmetry or presentation of a broad region of bifurcation 34 could result in turbulent or asymmetrical blood flow that could lead to development of blood clots or other obstruction. The first and second tubular branches 28, 30 are attached to each other by one or more sutures 32 to maintain the tubes 28, 30 in close, generally parallel relation.

The trunk 14 includes a supporting frame, illustrated generally at 36 in FIG. 6. The frame 36 is connected to the graft 22 and serves to maintain the graft 22 in its open configuration as the trunk 14 is released within the artery. In the preferred embodiment, the frame 36 may include an anchor 38 at its upper end and a stent 40 at its lower end. The anchor 38 and stent 40 may be formed from a suitable wire such as MP35N alloy in a zigzag configuration as illustrated in FIG. 4, including a plurality of alternating straight sections 42 and bends 44. The anchor and stent may be formed by first bending the wire into the zigzag configuration and then connecting the free ends 46 together, as by welding (FIG. 5) to define a ring-like configuration. Although omitted for clarity of illustration in FIG. 6, the anchor 38 may be provided with hooks, indicated generally at 48 as illustrated in FIGS. 1 and 3. The stent 40 is not intended to engage tissue and need not be provided with hooks 48 for that purpose. The lower ends of the stent 40 may protrude downwardly out of the legs 28, 30 and may serve as a connector to the delivery device.

By way of dimensional example, in the device intended for placement in an adult abdominal aorta, the overall length of the trunk 14 may be of the order of about six cm long, with the upper single lumen part 24 of the trunk being about three cm long and the lower portion 26 of the trunk also being about three cm long. The anchor 38 and stent 40 may be of the order 2.5 cm long so that when they are attached to the graft 22, the adjacently facing ends of the anchor 38 and stent 40 contained within the graft 22 will be spaced from each other to define an internal exposed cylindrical band 37 of uninterrupted graft material. The internal surface characteristics of the graft material preferably are such as to facilitate secure engagement with the leg extensions 16, 18 when the leg extensions are connected to the trunk 14, as described in further detail below. The large single lumen portion 24 of the trunk 14 may be of the order of fourteen to thirty mm in diameter. The diameter of the first and second tubular segments 28, 30 of the trunk may each be approximately half of that of the single lumen segment, that is, of the order of seven to fifteen mm. In a specific example, a trunk was made having a single lumen diameter of approximately 30 mm in diameter and a branch lumen diameter of approximately 14 mm. The anchor 38 is formed to define a relaxed diameter that is slightly greater than the diameter defined by the single tube portion 24 of the trunk to assure that the anchor will expand the open end of the graft fully. Similarly, the stent 40 is constructed to define a relaxed diameter that will assure full expansion of the branches 28, 30 and lower portion 26 of the endoprosthesis.

The frame 36 also preferably includes a connection between the anchor 38 and stent 40 in the form of elongate struts 50. In the illustrative embodiment, one end of each of the struts 50 is attached to the stent 40, as by welding. The other end of each of the struts is connected to the anchor 38, as with sutures 52 that also secure the struts to the graft 22. The struts 50 which, preferably, are located exteriorly of the graft 22, also may be attached along their lengths to the exterior surface of the graft 22, as by heat bonding. The struts 50 should be connected to the anchor 38 and stent 40 in a manner that will reduce the risk of development of stress concentrations on the frame when the device is flexed at any time during its use. To that end, in the illustrative embodiment, the struts 50 may be attached, as described below, as by welding to the stent 40 and by sutures 52 that also serve to attach the anchor 38 and stent 40 to the graft 22.

FIG. 7 shows, in greatly enlarged cross-sectional detail, the construction for the struts 50. The struts preferably include an inner core wire 54 surrounded by a helical coil 56 wrapped tightly about the core wire 54. The coil is wrapped in a thin tube of thermoplastic polymeric material 58. The polymeric layer may comprise polypropylene, applied as a tube about the coil 56 and then heated sufficiently to cause the polypropylene to begin to melt and flow into close intimacy with the turns of the coil 56 and the graft 22. The polymeric layer 58 may be formed from a lower melt temperature polymeric material from that of which the graft 22 is formed. By bonding the polymeric covering directly to the graft material, as suggested in FIG. 7, the struts may be attached securely along their full lengths to the graft 22 to provide full longitudinal support for the graft 22. The struts 50 also serve to prevent the graft 22 from becoming twisted in that the struts, being substantially straight and resilient, will resist such twisting. The core wire 54 and wire from which the coil 56 is formed may be formed from MP35N alloy. The construction of the struts provides enhanced longitudinal rigidity and column strength after the device is assembled and during deployment, while at the same time allowing the device to collapse to a low profile. A strut so constructed may have sufficient radiopacity to permit adequate X-ray or fluoroscopic visualization of the struts when implanted in the abdominal aorta. The radiopacity of the struts may be enhanced by adding a radiopaque filler material to the polymeric material 58.

Although, in this embodiment, the lower, trailing end of the trunk 14 includes a pair of branch tubes 28, 30, a single stent 40 can be used to maintain both tubes 28, 30, in an open configuration when the device is deployed. The zigzag construction of the stent 40 is such that the adjacent portions 60 of the lower ends of the tubes 28, 30 can be placed between opposed pairs of straight sections 42 of the stent 40. FIG. 3 illustrates such an arrangement in which the adjacent straight sections 42a, 42b and opposed straight sections 42c, 42d embrace the adjacent portion 60 of the first and second tubes 28, 30. When the lower end of the trunk in this embodiment is relaxed and permitted to expand, the cooperation between the attached tubes 28, 30 and the stent 40 defines a generally oval cross-sectional configuration that includes the open adjacent tubes 28, 30. FIG. 6 illustrates the configuration of the frame with the stent 40 defining the generally oval shape. One or both of the tubes 28, 30 may be provided with radiopaque means for enhancing fluoroscopic visualization of the openings of the tubes 28, 30. Such means may, for example, be in the form of a ring of radiopaque material.

By way of further example, an anchor 38 adopted for use in an adult aorta may have twelve straight sections 42 disposed at an angle to each other of about 30°, when relaxed. It should be understood, however, that the dimensions and number of wire segments 42 of the anchor 38 may be varied, depending on the size of the lumen into which the endoprosthesis is to be placed and the specific condition to be treated. The diameter defined by the anchor should not be less than that of the body lumen into which it is to be deployed in order that the anchor may expand the graft fully into firm and sealed engagement with the body lumen. Preferably, the expanded diameter defined by the anchor may be slightly greater than that of the body lumen. When the device is advanced to the site where it is to be implanted, it is released from the delivery device and, as it is released, the anchor expands to a larger diameter and into engagement with the inner surface of the body lumen. In the illustrative embodiment, the anchor 38 presses radially outwardly against the inner luminal surface of the aorta and serves to retain the trunk in place.

The security of the engagement between the trunk 14 and the blood vessel wall preferably is enhanced by providing hooks 48 on the upper anchor 38. The hooks 48 are formed on the upper ends of hook supports 47. The hook supports 47 preferably are formed from the same material as the wire of the anchor 38, and may be attached to and along the straight sections 42 of the anchor 38. The hook supports 47 and hooks 48 are arranged with the hooks 48 disposed above the bends 44 of the anchor 38. The hook supports 47 preferably are welded to the straight sections of the anchor at two junctions. The hooks 48 preferably are sharp and extend radially outward so that they can dig into the vessel to prevent migration of the device. The hooks 48 may be oriented at a downward angle to present substantial resistance to shifting of the upper anchor 38 in a downstream direction. The hooks 48 are arranged so that when the device is deployed, the hooks 48 will project radially outwardly beyond the outer portions of the endoprosthesis to assure that the hooks will engage securely the tissue of the blood vessel.

It is desirable that the device be constructed so that the anchor 38 can be contracted to a low profile configuration in which the implant is insertable into and carried by the tubular pod 19 of the delivery device 15 but without the hooks 48 becoming entangled with each other or otherwise interfering with the ability of the device to be radially contracted or expanded. To that end, the hooks are supported in a manner such that they will extend radially outwardly of the upper end of the delivery device when the implant is deployed but can be withdrawn radially inwardly into the pod of the delivery device when the implant is contracted. FIGS. 3 and 8–10 illustrate a preferred arrangement by which the hooks may be provided with such radial movement. To that end the hook supports 47 are shaped to include an S-shaped region that defines transverse extensions E, F that can engage the rim 21 at the leading end of the pod 19 as the anchor 38 is drawn, relatively, into the pod 19. The S-shaped portion 62 of the hook support 47 may lie essentially in a single plane (see FIG. 9) that includes a center line 66 of the hook support 47 and extends approximately tangentially to the outer periphery of the anchor 38. The extent to which the transverse extensions E, F extend from the center line 66 may be varied depending on the other dimensional requirements of the system. The transverse extensions should define a distance E+F that will assure the retraction of the hooks 48 to their intended radially inwardly disposed configuration so that they can be captured within the pod 19, without entanglement, as suggested in FIG. 10. When the rim 21 of the pod 19 engages the transverse extensions E, F of the hook supports 47, advancement of the pod 19 will depress and urge the hook supports 47 radially inwardly to cause the ends of the hooks 48 to be drawn radially inwardly toward the central axis of the anchor. The chordal segment defined by the length E +F should be such that the radial projection J of the hook 48 will be well within the circumference defined by the inner diameter of the pod 19. Reference is made to European patent application, publication number EP701800A1, for additional description of the arrangements for effecting radial movement of hooks in response to engagement of the advancing pod.

Figure 14:
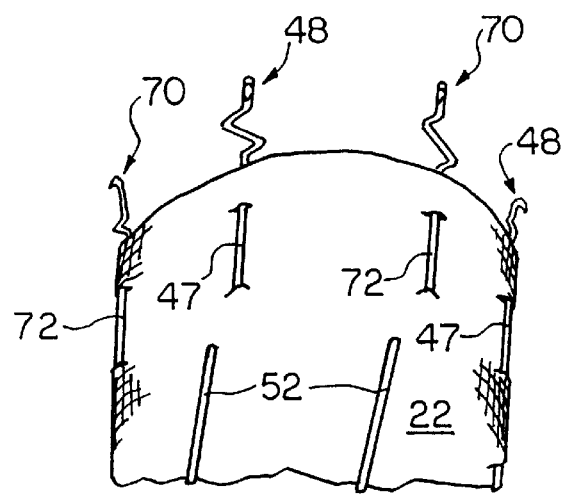
FIG. 14 is an illustration of the upstream end of a trunk embodying alternating hooks to resist downstream movement and detents to resist upstream movement of the endoprosthesis.

It also may be desirable to include vessel-engaging members that will prevent shifting of the implant in an upstream direction. To that end and as shown in FIGS. 11–14 the anchor 38 also may be provided with detents 70 that may be formed on the upper ends of each of one or more detent supports 72 in the same manner as the hooks 48 are disposed on the hook supports 47. The detent supports 72 also may be provided with transverse extensions E' and F' to facilitate their controlled radial retraction when the pod 19 is advanced to recapture the trunk. The detent 70 may be formed simply by providing a bent tip 74, at the upwardly extending ends of the supports 72, beyond the transverse extensions. The bent tip 74 preferably is formed at an acute angle to the center line 76 of the support 72. By way of dimensional example, the bent tip 74 may be of the order of about 0.08" long and may extend radially outwardly by a dimension K about 0.04 inch from the center line 76. The uppermost end of the tip may be beveled, as indicated at 78, to provide a sharp point oriented to dig into the tissue of the blood vessel should the device tend to shift in an upward direction. It should be noted that when the device is deployed the detents will press radially outwardly against the tissue of the vessel. The sharp tips will not fully dig into the tissue of the vessel unless and until the device is urged in an upstream direction. The anchor 38 may be configured to have alternately downstream resistant hooks 48 and upstream resistant detents 70 as shown in FIG. 14.

The stent 40 may be assembled and integrated with the graft 22 by first attaching the lower ends of the inner core wires 54 to straight sections 42 of the stent 40, preferably in a manner that will avoid the development of significant stress concentrations at the region of attachment. In the illustrative embodiment, the lower ends of the inner core wires 54 may be spot welded, as suggested at 53 in FIG. 4A. After the lower ends of the core wires 54 have been so attached, the stent 40 is placed in the open ends of the branch tubes 28, 30, passing the free ends of the inner core wires 54 from the inside to the outside of the graft 22 through small holes 51 formed in the branch tubes 28, 30. With the stent 40 positioned in the graft 22 as described with the core wires 54 protruding outwardly through the graft 22, the helical coils 56 are slipped onto the core wires 54 and the polymeric tubes 58 are slipped over the helical coils 56. After the anchor 38 is assembled with its arrangement of hooks 48 and, if employed, detents 70, the anchor 38 is placed within the upper end of the graft 22, with the hooks 48, hook supports 47, detent 70 and detent support 72 being manipulated through small openings 53 formed about the upper end of the graft 22. The sutures are placed to further connect the anchor 38, stent 40, struts 52 and graft 22 together. The polymeric tubes 58 then may be heat bonded to the graft 22. It may be noted that the upper ends of the struts 50 need not be rigidly attached to the anchor 38 and, preferably, are attached to permit flexibility between the two without developing adverse stress concentrations. To that end, the sutures 52 associated with the anchor 38 provide a connection between the anchor 38 and the struts 50 while also serving to attach the anchor 38 to the graft 22. The sutures 52 associated with the anchor 40 serve to provide an additional connection between the frame 36 and the graft 22.

Figure 19:
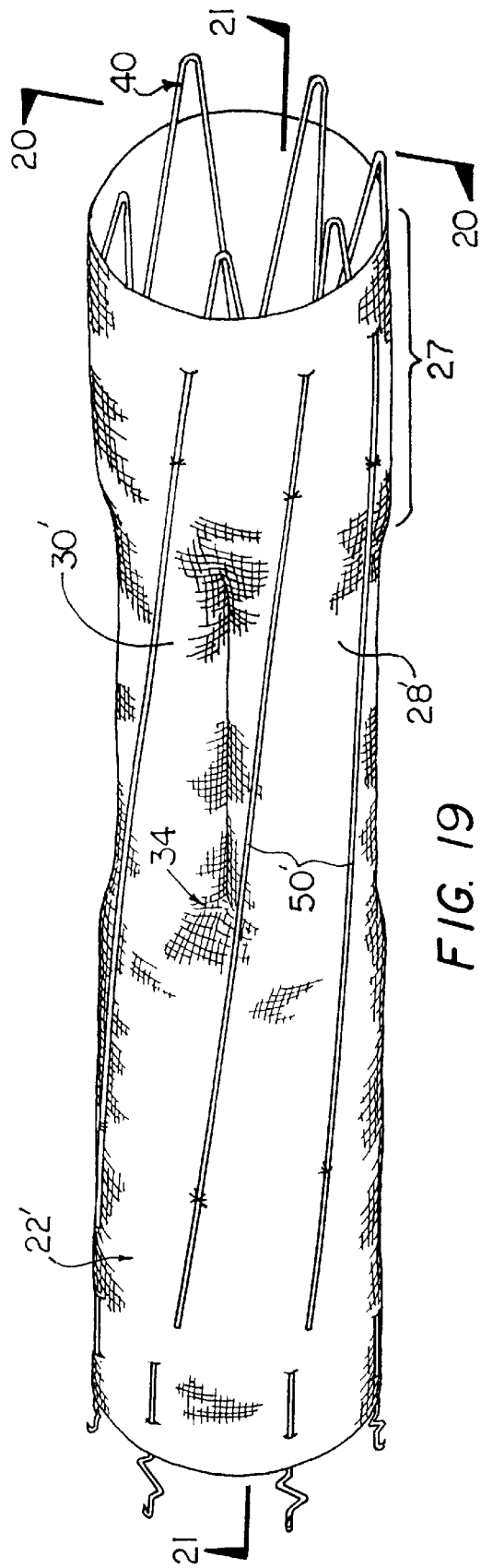
FIG. 19 is an illustration of a modified embodiment of the trunk module of the invention.
Figure 21:
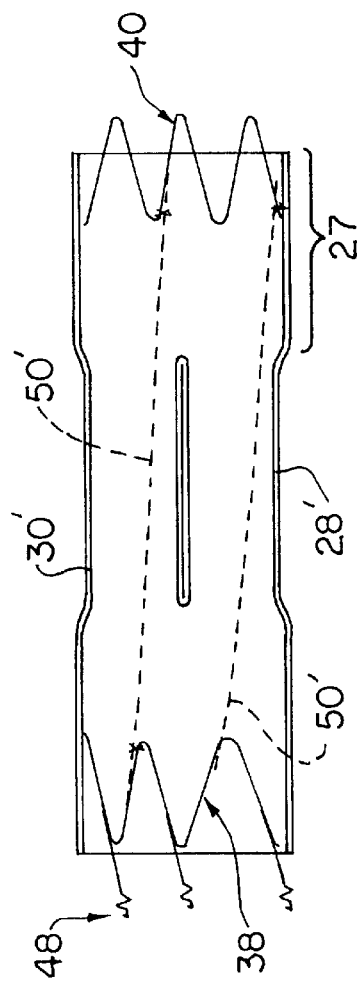
FIG. 21 is a reduced scale, longitudinal cross-section through the trunk of FIG. 19 as seen from 21—21 of FIG. 19.
Figure 20:
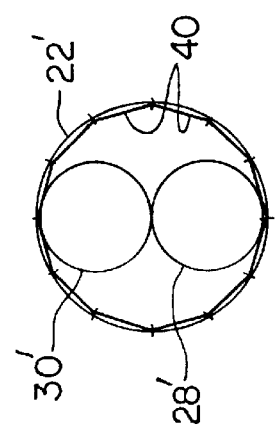
FIG. 20 is an end view of the lower end of the trunk as shown in FIG. 19 as seen from 20—20 of FIG. 19.

FIGS. 19–21 illustrate a modified embodiment of the anchor that may be constructed in similar fashion to that described above in connection with the embodiment of FIG. 3. In this embodiment, the graft 22' is formed to include an additional single lumen segment 27 having an expanded diameter approximately equal to the sum of the diameters of the first and second branch tubes 28', 30'. The stent 40 may be the same stent as that described above in connection with the embodiment of FIG. 3. The single lumen configuration of the segment 27 enables the stent 40 to expand that segment to a generally circular cross-section (FIG. 20). The struts 50' may be constructed in the same manner discussed above. The device thus may be considered to include a pair of generally circular cross-section lumens at its ends that communicate with a pair of smaller diameter parallel lumens defined by the tubes 28', 30'. As described below in connection with the description of the manner in which the device is used, the enlarged diameter opening defined by the segment 27 presents a larger target to facilitate coupling of the leg extension 16, 18, with the trunk.

As shown in FIGS. 15–18, each of the leg extensions 16, 18 may include a flexible outer tube 90 of the type commonly used as a synthetic blood vessel. Although other constructions may be employed, in a presently preferred embodiment the tube 90 may be formed from a conventional graft material, such as a fabric similar to the fabric from which the graft 22 is formed. It should be understood, however, that any of a variety of conventional graft materials may be employed including graft materials that have differing characteristics than other of the modular components in order to suit the particular requirements of the patient. The length of the graft 90 may be varied to suit the anatomy of the particular lumens into which the implant is to be placed. The tube 90 is supported internally by a stent 92 that, in the preferred embodiment, extends substantially the full length of the tube 90. The lower end of the extension leg 16, 18 may be provided with a means by which it can be engaged by the delivery catheter to enable the leg extension to be recaptured, for repositioning or removal before release, should that be desired. To that end lower end of the stent 92 may protrude downwardly beyond the lower end 91 of the tube 90 and preferably defines, when relaxed, a slightly flared configuration defining a plurality of downwardly facing projections 94. Stent 92 is expandable from a low profile configuration (FIG. 15) in which it can be received within the tubular pod 19 of the delivery device and an expanded configuration in which it has fully expanded the graft 90. Although a number of stents may be employed, it is presently preferred to use the type of stent described in German patent number 43 03 181.1 issued to Angiomed A G of Karlsruhe, Germany and from whom such stents are available commercially.

The leg extensions 16, 18 are deployed with the use of a delivery catheter such as that described above in connection with the trunk 94 and incorporated by reference herein. One of the leg extensions 16, 18 is carried by the delivery device to a position in which the leg extension is disposed within one of the branch tubes 28, 30 of the previously placed trunk 14. While maintaining the position of the leg extension, the sheath and pod 19 are withdrawn to progressively enable the stent 92 to expand the tube 90 within and into engagement with the inner surface of the trunk 14. The leg extensions 16, 18 are selected to have an expanded diameter to match the internal dimensions of the trunk 14 so that the upper end of the leg extension, when released, will firmly and securely engage the inner luminal surfaces of the trunk 14. The dimensions and engagement should be such as to assure a firm and secure contact between the inserted end of the leg extensions to prevent separation of the leg extension from the trunk 14 as well as to provide a seal between the two to prevent blood from leaking out of the implant. The preferred embodiment the leg extensions are secured by cooperative engagement of the facing surfaces of the tube 90 and the inner surface of the graft 22 coupled with the radial expansive force with which the stent 92 presses the tube 90 against the interior of the truck 14. Preferably a substantially region of surface-to-surface engagement will result between the coextensive circumferential band 37 of graft material 22 of the trunk 14 with the external engaged surface of the upper end of the tubular graft 90.

Depending on the configuration at the lower end of one or more of the modules, it may be desirable to provide a delivery device modified somewhat from that described in European published application No. EP 0 701 800 A1, particularly with the manner in which the lower (trailing) end of the module is held. As shown in FIGS. 22–24, the modified delivery device includes an arrangement of an outer flexible tube 96 that defines a slightly enlarged diameter sheath 98 at its distal end. Disposed coaxially within the outer tube 96 is an intermediate tube 100 that is slidably longitudinally within the outer tube 98 and has a distally opening cup 102 at its distal end. A metal inner tube 104 is disposed coaxially within the intermediate tube 100 for longitudinal movement with respect to the intermediate tube 100. The inner tube has an enlarged member 106 attached at a location that the member 106 can be disposed within the cup 102 (FIG. 23) or extended distally beyond and out of the cup 102 (FIG. 24). The cross-sectional dimensions of the member 106 and the inner surface of the cup 102 are such that when brought together they can cooperate to wedge the trailing end of a radially contracted endovascular modular component such as a leg extension 16, 18 between the member 106 and the cup. As illustrated diagrammatically in FIG. 23, the trailing end of the leg extension 16 is securely gripped in the generally annular space between the member 106 and the cup 102. The grip should be secure to assure that the trailing end of the endoprosthesis will not be released inadvertently so that the endoprosthesis can be recaptured, should that be desired. FIG. 23 illustrates the relative configuration of the components after the outer tube 96 has been withdrawn sufficiently to withdraw the sheath 98 to project the gripped, trailing end of the endoprosthesis 16 out of the sheath. When the physician is satisfied that the endoprosthesis 16 has been placed as desired, the intermediate and inner tubes 100, 104 can be moved relative to each other to release the endoprosthesis 16 so that the endoprosthesis can expand (FIG. 24).

The position of the tubes 96, 100, 104 may be controlled by conventional lockable fittings at the proximal end of the device. As shown in FIG. 22 a fitting 108 is attached to the proximal end of the tubular shaft 96. The intermediate tube 100 extends through the fitting 108 and itself has a fitting 110 at its proximal end. The inner tube 104 extends through the fitting 1 10 and has another fitting 112 attached to its proximal end. The fitting 112 is constructed to enable a guidewire (not shown) to be inserted through the lumen of the inner tube 104.

Figure 25D:
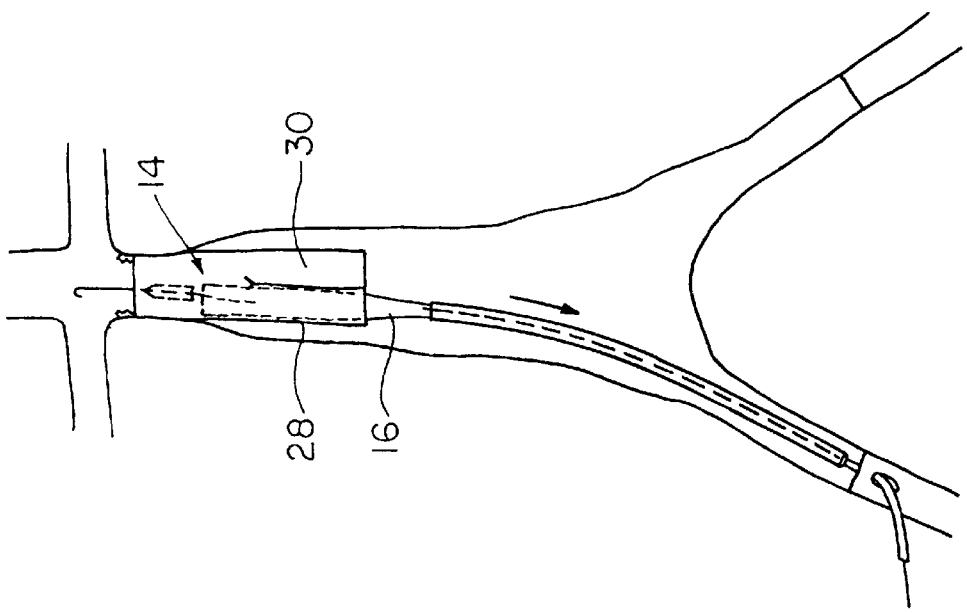
Figure 25C:
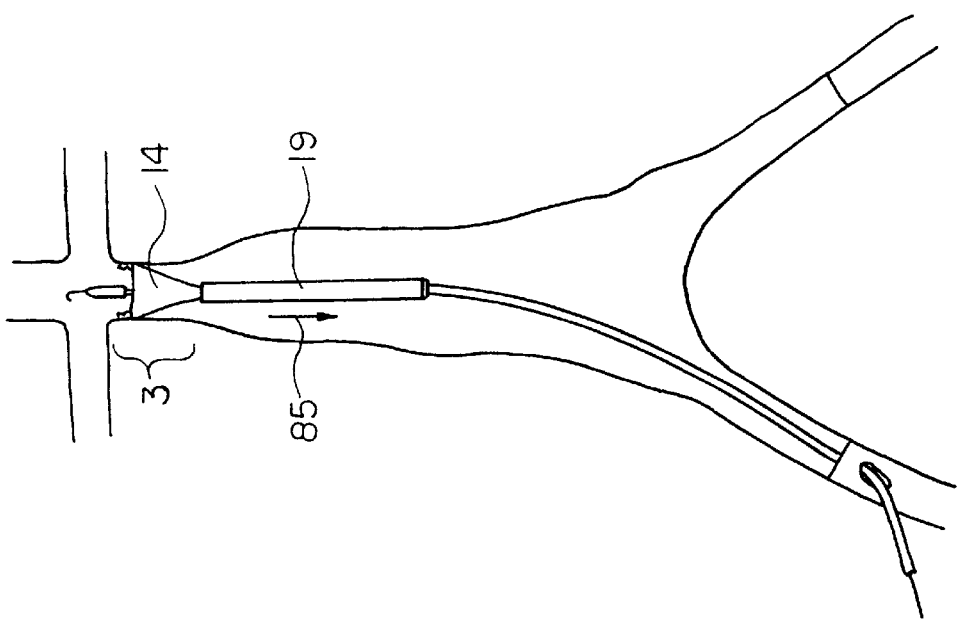
Figure 25F:
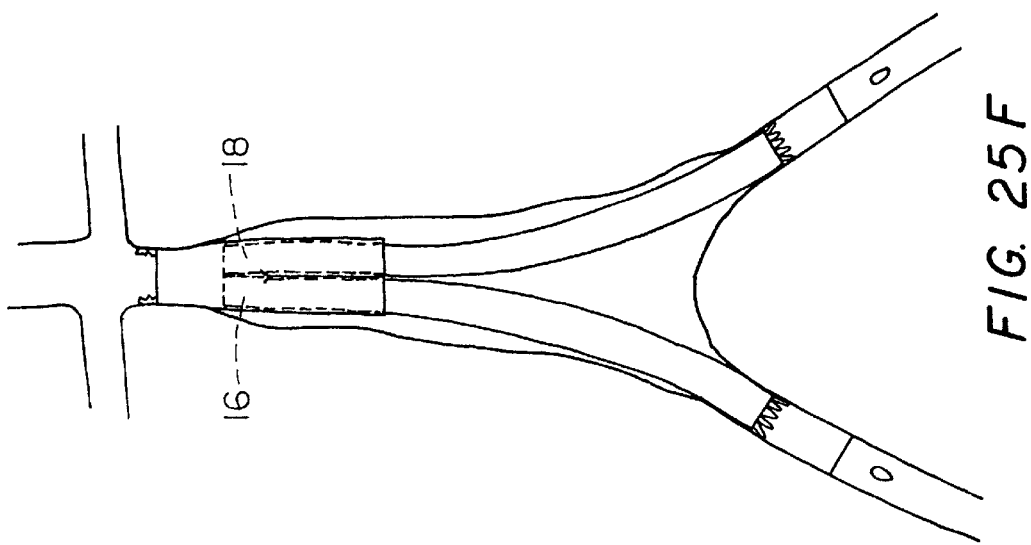
Figure 25E:
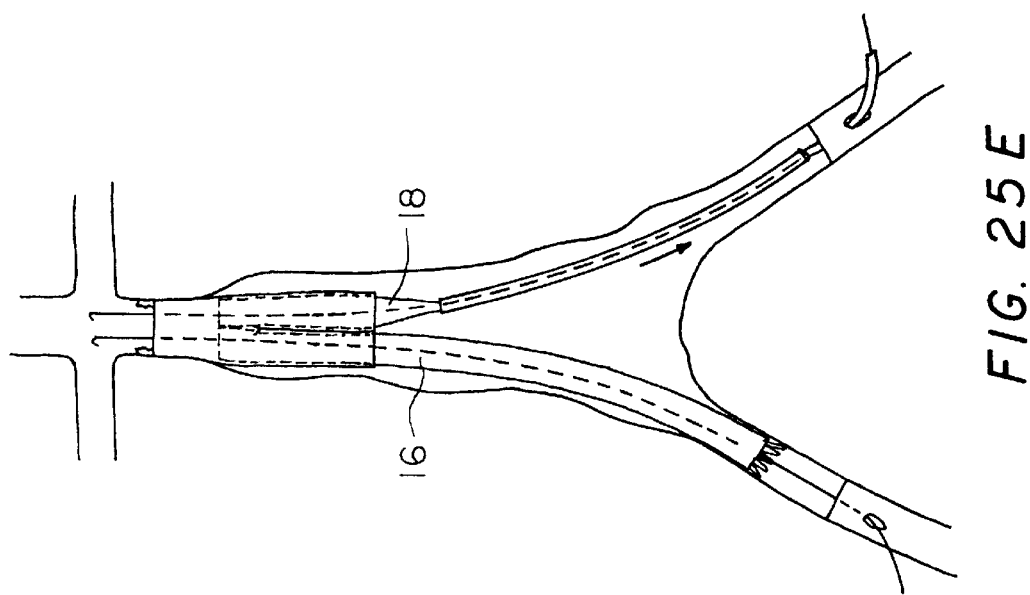

FIGS. 25A–25F illustrate, diagrammatically one sequence of the operations by which the modular endoprosthesis may be deployed. FIG. 25A illustrates, diagrammatically, a portion of a patient's abdominal aorta 2 and several branch vessels, including the renal arteries 6 and iliac arteries 8. The aneurysm 12 is illustrated as having extended into and beyond the bifurcation 10, to include a portion of the iliac arteries 8. FIG. 25A illustrates an access opening 82 formed in one of the iliac arteries 8. The access opening 82 may be formed percutaneously or in a surgical cut-down technique. Typically, an introducer sheath (not shown) will be placed through the opening 82 to receive the various instruments and permit their manipulation without subjecting the patient to excessive trauma. FIG. 25A illustrates the patient anatomy with a guidewire 84 having been placed to extend upwardly to and through a region of healthy aortic tissue 3 above the aneurysm 12. With the guidewire 84 in place, the delivery device, which includes a guidewire lumen, is advanced over the guidewire 84 until the pod 19 at the distal end of the sheath 17, which contains the trunk 14 in a low profile, contracted configuration, is located at the intended placement site. When the physician is satisfied that the pod 19 and trunk 14 are at the desired location (FIG. 25B), the delivery catheter 15 is manipulated to maintain the position of the trunk 14 relative the patient's vasculature, while withdrawing the sheath 17 and pod 19, as indicated by the arrow 85 in FIG. 25C. The desired position of the trunk 14, before deployment, is such that the anchor 38, including its hooks 48 and detents 70, will be disposed within healthy tissue capable of firmly supporting the upper end of the trunk 14. As suggested in FIG. 25C, as the sheath 19 is withdrawn, the trunk 14 is progressively exposed to enable the anchor 38 to expand the endoprothesis toward an expanded diameter so that it will firmly and securely engage the region 3 of healthy aortic tissue above the aneurysm 12.

Should it be necessary reposition or withdraw the trunk 14, even after its anchor 38 has engaged the healthy tissue 3, that can be accomplished at any time before complete release by simply readvancing the sheath and pod 19 upwardly over the trunk 14. As the rim of the sheath 19 engages the transverse extensions, the hooks 48 and detents 70 are retracted radially inwardly within the circumference of the rim of the pod 19 so that further advancement of the pod will fully enclose the hooks 48 and detents 70 in the manner suggested in FIG. 10. After the physician is satisfied that the device is in the desired positioned and orientation, the delivery catheter is manipulated to release the trailing end of the trunk 14.

Figure 26E:
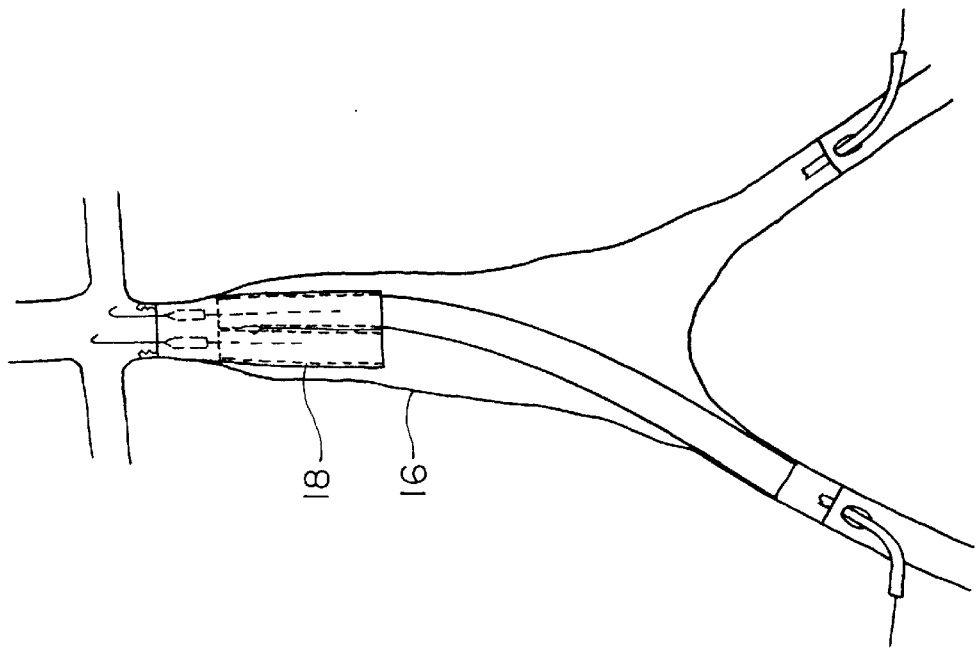
FIGS. 26D–26G illustrate, schematically, a modified procedure of sequential steps in the placement of the endoprosthesis.
Figure 26D:
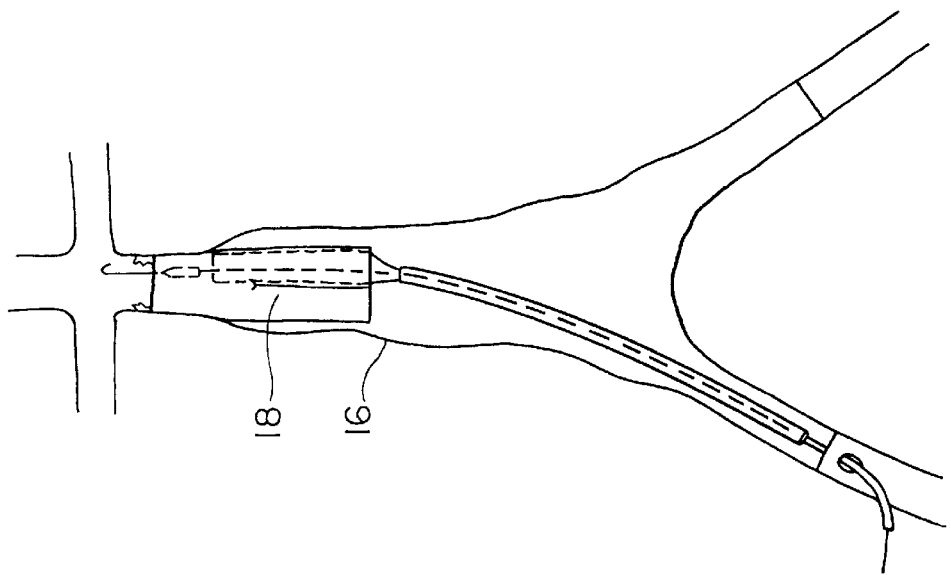

FIG. 26D illustrates the configuration of the trunk 14 after it has been released. In this configuration the trunk 14 is attached to the healthy aortic tissue only by the anchor 34. The lower end of the trunk 14, including the lower ends of the bifurcated tubes 28, 30 depend downwardly but without support of engagement with any part of the body lumen. The construction of the trunk is such that it has sufficient longitudinal stiffness and the open lower ends are supported by the stent 40 so that it has sufficient rigidity to be self supporting and readiness to receive leg extensions 16,18. After the trunk 14 has been deployed the delivery device is removed from the patient. In one method of deployment, the guidewire 84 may remain in place in order to serve as a guide for delivery device for one of the leg extensions 16, 18.

From foregoing it will be appreciated the trunk 14 serves as a first, securely placed component of the endovascular prosthesis. The trunk 14 is configured to present a stable pair of targets in the form the open lower ends of the branch tubes 28, 30 in order to facilitate advancement of the leg extensions into the branch tubes 28, 30. The frame associated with the trunk 14 provides a firm stable shape for the trunk 14 that will be unaffected by engagement of the delivery device for the leg extensions. The trunk 14 provides continuous wide inlet openings to receive the upper, leading ends of the leg extensions 16, 18. The lower openings of the branch tubes 28, 30 may be provided with radiopaque markers, as in the form of rings 29 or the like by which the entry openings of the branch tubes 26, 28 can be visualized fluoroscopically.

The placement of the leg extensions 16, 18 may be performed in essentially the same manner as the placement of the trunk 14, that is, by a catheter-like delivery device adapted to contain a leg extension in a low profile configuration, in readiness for expansion when released. After the trunk 14 as been placed, a delivery device is loaded with one of the leg extensions 16, 18. The delivery device then can be advanced over the initially placed guidewire 84 until its leading, upper end is disposed, as desired, within the trunk 14. As shown in FIGS. 17 and 18 the leg extension may be advanced into a receptive of the branch tubes 28, 30 to dispose the upper end of the inserted leg extension beyond the stent 40 and into the intermediate 37 between the stent and anchor. As described, the surface characteristics of the outside of the tube 90 and the interior of the trunk, including the internal surfaces of the graft material 22 should be selected so that a secure and sealed connection will be formed when the tube 90 is in its expanded configuration, connected to the trunk 14. When the leg extension is so placed, the sheath and pod of the delivery device 15 are withdrawn to enable the leg extension to expand and with it's upper portion and secure overlapped engagement with the trunk 14. As the sheath and pod are progressively withdrawn the exposed portion of the stent can expand to it's expanded diameter. The length and diameters of the leg extension are selected so that the upper end will securely engage the trunk and the lower end will expand into firm engagement with healthy tissue of the iliac artery 8, below the aneurysm 12. Presently preferred embodiment, the lower of the leg extensions include the downwardly and radially outwardly extended projections adapted to engage healthy tissue of the iliac arteries. When the delivery device has been withdrawn, the projections will remain in engagement with healthy iliac artery tissue.

Figure 26G:
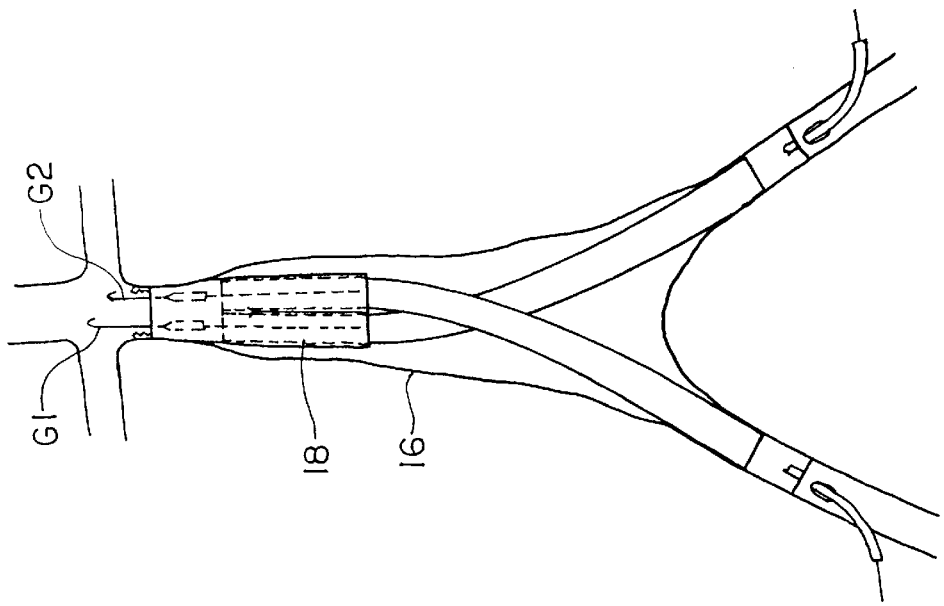
Figure 26F:
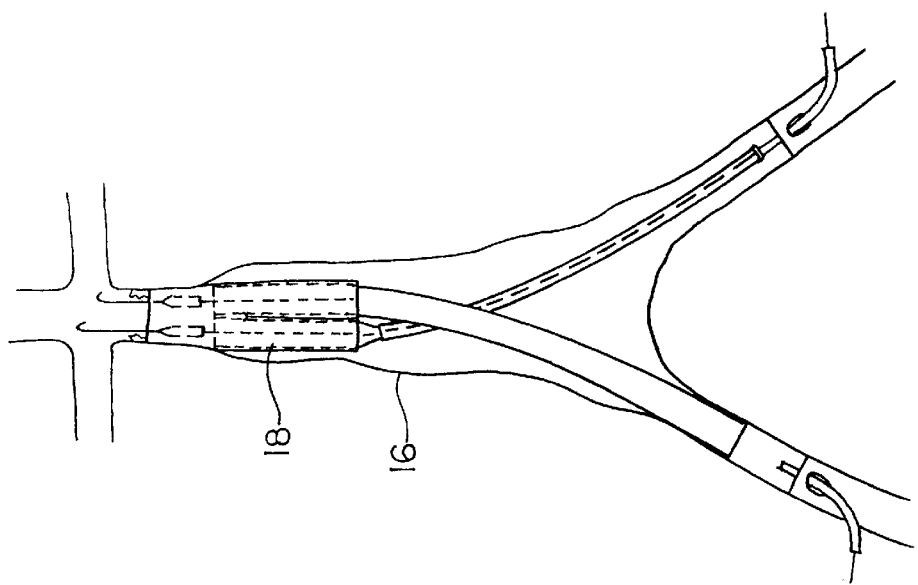

The in vivo construction of the bifurcated graft then can be completed by placing another guide wire 86 in the other iliac artery and advancing it upwardly through the other of the bifurcated tubes 28, 30. The delivery device, loaded with the other leg extension than can be advanced in the same manner as the first leg extension and deployed in the same manner. FIG. 26E illustrates the withdrawal of the delivery device as the other leg extension expands progressively. FIG. 26F illustrates the bifurcated endoprothesis, constructed in modular fashion after removal of the guide wires and delivery devices.

FIGS. 26D–26F illustrate a modified procedure for placing the modular endoprosthesis. The modified procedure begins the same as that described above in connection with FIGS. 26A–26C. The next step, of delivering and deploying one of the leg extensions 16, 18, is substantially similar in this modified procedure except that instead of directing the guidewire and delivery device into the bifurcated branch of the trunk on the same side as the iliac artery that was accessed, the delivery device is directed to the branch tube 30 on the opposite side. By so doing, the placement of the initial guidewire and the delivery device is facilitated in that the branch tube 30 on the opposite side can be expected to be more directly in line with the iliac artery through which the device was placed. FIG. 26D illustrates the first of the two leg extensions having been so cross-placed. FIG. 26E illustrates the system after the leg extension has been attached to the trunk and the delivery device has been withdrawn, leaving one of the leg extensions in place connecting the trunk and its associated iliac artery. FIG. 26F illustrates the similar placement of the other leg extension, showing the delivery device having partially deployed the leg extension in the other of the branch tubes. FIG. 26F illustrates that the cross-placement results in the devices being crossed within the aneurysmal region. FIG. 26G illustrates the configuration after the second of the leg extensions has been fully deployed to directly connect its associated branch tube of the trunk with its associated iliac artery. It should be understood that variations of this modified procedure may be employed. For example, it may be desirable to first deploy both guidewires G1, G2 in a cross-configuration. Then, with the guidewires in place, the delivery devices may be advanced over the guidewires and the module deployed.

Figure 27:
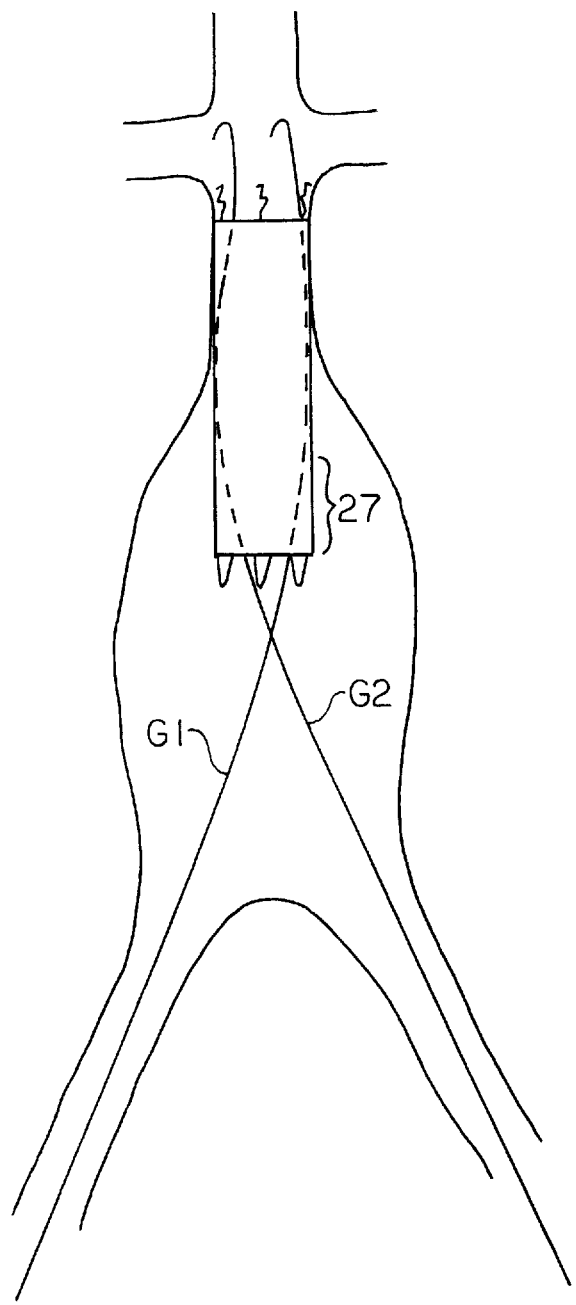
FIG. 27 is a diagrammatic illustration of the manner in which the modified trunk of FIG. 19 may be placed.

FIG. 27 illustrates, diagrammatically, the manner in which the modified trunk shown in FIG. 19 may be used in the practice of the invention. The placement and deployment of the trunk itself as well as the leg extensions is essentially identical to the modes described above. The addition of the lower segment 27, however, provides a larger tubular target for the guidewires, illustrated diagrammatically as G1 and G2. The physician may find it easier to place the guidewire within the larger diameter lower extension than if the target were the smaller diameters as defined by the branch tubes 28, 30. The distal ends of the guidewires typically will be provided with an atraumatic J-shape. Use of the cross-over technique described above in connection with FIGS. 27D–27G may be employed, as shown.

It should be understood that the foregoing description of the invention is intended merely to be illustrative thereof and other embodiments, modifications and equivalents will be apparent to those skilled in the art without the departing from the principles of the invention.

Having thus described the invention what we desire to claim and secure by Letters Patent is:

1. An apparatus for delivering and deploying a radially expandable tubular implant within a body vessel comprising:

a tubular sheath for maintaining the radially expandable tubular implant in a radially contracted configuration, the sheath having a proximal end and a distal end and being open at its distal end and axially movable relative to the implant;

a gripping device disposed within and movable longitudinally of the sheath, the gripping device being constructed to releasably grip the trailing end of the implant;

the gripping device further comprising a cup having a distally facing open end adapted to receive the trailing end of the implant and a gripping member movably mounted with respect to the cup between a gripping position in which the gripping member is withdrawn into the cup to define an annular space between its periphery and the interior of the cup and a release position in which the gripping member is disposed out of the cup;

the annular space being sufficiently narrow to enable the trailing end of the implant to be securely wedged between the gripping member and the cup when the gripping member and cup are in the gripping position;

wherein the gripping member is axially movable with respect to the implant by axial remote movement of an inner member attached to the gripping member such that the implant is released from its wedged securement in the annular space.

\* \* \* \* \*